(12) United States Patent
Gamsey et al.

(10) Patent No.: US 8,178,676 B2
(45) Date of Patent: May 15, 2012

(54) PYRIDINIUM BORONIC ACID QUENCHERS FOR USE IN ANALYTE SENSORS

(75) Inventors: Soya Gamsey, Huntington Beach, CA (US); Ritchie A. Wessling, Watsonville, CA (US)

(73) Assignee: Glumetrics, Inc., Irvine, CA (US)

( * ) Notice: Subject to any disclaimer, the term of this patent is extended or adjusted under 35 U.S.C. 154(b) by 0 days.

(21) Appl. No.: 13/069,150

(22) Filed: Mar. 22, 2011

(65) Prior Publication Data

US 2011/0171742 A1 Jul. 14, 2011

Related U.S. Application Data

(62) Division of application No. 12/113,876, filed on May 1, 2008, now Pat. No. 7,939,664.

(60) Provisional application No. 60/915,372, filed on May 1, 2007.

(51) Int. Cl.
*C07F 5/02* (2006.01)
*G01N 33/66* (2006.01)
(52) U.S. Cl. .............................. 546/13; 436/14; 424/9.1
(58) Field of Classification Search .................... 546/13; 436/14; 424/9.1
See application file for complete search history.

(56) References Cited

U.S. PATENT DOCUMENTS 7,470,420 B2 12/2008 Singaram et al.

FOREIGN PATENT DOCUMENTS

| WO | WO 02/46752 A2 | 6/2002 |
| WO | WO 2007/067743 A2 | 6/2007 |
| WO | WO 2008/014280 A2 | 1/2008 |

OTHER PUBLICATIONS

Cappuccio, F.E. et al. 2004 "Evaluation of pyranine derivatives in boronic acid based saccharide sensing: Significance of charge interaction between dye and quencher in solution and hydrogel" *Journal of Fluorescence* 14:521-533.
Gamsey, S. et al. 2006 "Continuous glucose detection using boronic acid-substituted viologens in fluorescent hydrogels: Linker effects and extension to fiber optics" *Langmuir* 22:9067-9074.
Sharrett, Z. et al. 2008 "Boronic acid-appended bis-viologens as a new family of viologen quenchers for glucose sensing" *Tetrahedron Letters* 49:300-304.
Suri, J. T. et al. 2003 "Continuous glucose sensing with a fluorescent thin-film hydrogel" *Angew Chem Int Ed* 42:5857-5859.

*Primary Examiner* — Charanjit Aulakh
(74) *Attorney, Agent, or Firm* — Knobbe Martens Olson & Bear LLP

(57) ABSTRACT

Novel pyridinium salts functionalized with boronic acid and methods of making them are disclosed. When combined with a fluorescent dye, the compounds are useful in the detection of polyhydroxyl-substituted organic molecules.

12 Claims, 1 Drawing Sheet

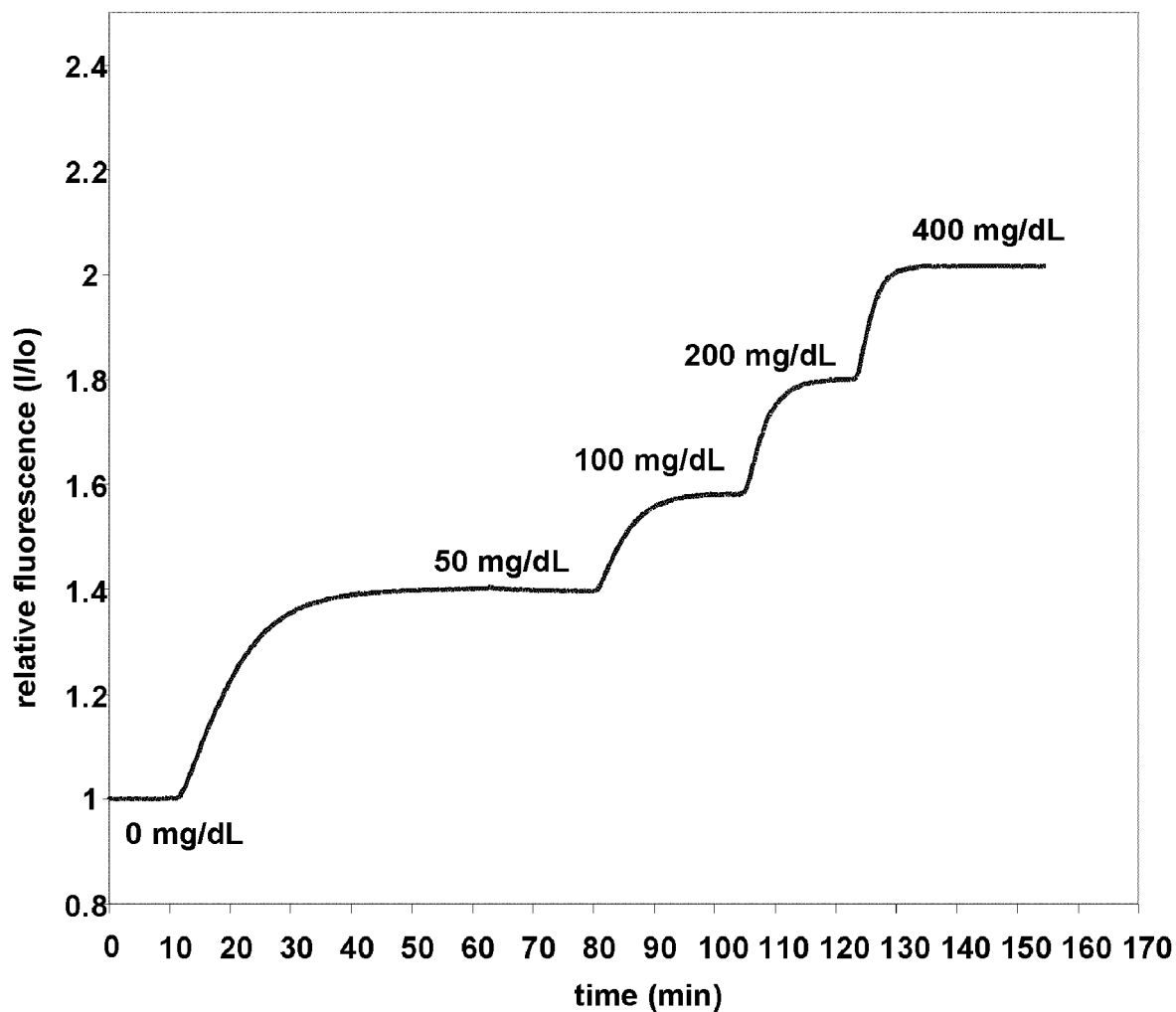

PYRIDINIUM BORONIC ACID QUENCHERS FOR USE IN ANALYTE SENSORS

RELATED APPLICATIONS

This application is a divisional of application Ser. No. 12/113,876, filed May 1, 2008, which claims the benefit of U.S. Provisional Application No. 60/915,372 filed May 1, 2007, which is hereby expressly incorporated by reference in its entirety.

FIELD OF THE INVENTION

The invention relates generally to the detection of polyhydroxyl-substituted organic molecules, and in particular to the use of pyridinium salts functionalized with boronic acids as quenchers of fluorescent dyes.

DESCRIPTION OF THE RELATED ART

Investigators have made fluorophores with N-benzyl-2-boronic acid pyridinium groups attached to a porphyrin ring (Arimori, S. et al. 1996 *J Am Chem Soc* 118:245-246). They were used to promote aggregation with another porphyrin substiuted with saccharide groups via intermolecular ester formation. Benzyl-2- and benzyl-4-boronic acid substituents on the pyridine nitrogens in substituted porphyrins were also described (Arimori et al. 1996 *Chemistry Letters* 25:77). They were used to distinguish chiral orientation in sugars. It was shown that the fluorescence was reduced by complex formation between these porphyrins and anthraquinone disulfonates. The complex was dissociated by reaction of the boronic acids with fructose resulting in an increase in fluorescence. The quenching moiety in this case was the anthraquinone component (Arimori et al. 1995 *J Chem Soc, Chem Commun* 9:961-962). Subsequently, investigators described a dye with a pyridine ring in the structure, substituted on the nitrogen with a benzyl-2-boronic acid group (Takeuchi et al, 1996 *Bull Chem Soc (Jpn)* 69:2613-2618). It was noted that the pyridinium group in ortho-position enhances reactivity of boronic acids with diols. This dye was used to detect nucleotides. In a paper concerning trialkyl ammonium substituted benzyl-2-boronic acids, a generic formula for N-benzyl-2-boronic acid derivatives of para-substituted pyridines was given, where the substituent was specified as an R-group (i.e., alkyl) (Takeuchi et al. 1996 *Tetrahedron* 52:12931-12940).

A pyridinium salt without a boronic acid substituent was used as a reference compound in a quenching study (Cordes et al. 2005 *Langmuir* 21:6540-6547). Other investigators measured the fluorescence quenching activity and glucose response of the three isomers of N-benzylboronic acid pyridinium salts. These compounds showed poor quenching of pyranine fluorescence and gave no glucose response (See e.g., "Detection of glucose with arylboronic acid containing viologens and fluorescent dyes: Progress toward a continuous glucose monitoring system for in vivo applications" Cappuccio, Frank E., Ph.D. Dissertation; UNIVERSITY OF CALIFORNIA, SANTA CRUZ, 2004).

A comparative study was reported on the quenching of Ru(bpy)$_3$ by methyl viologen (MV) and a series of 4-substituted N-methylpyridiniums (Jones and Malba 1985 *J Org Chem* 50:5776-5782). This study showed that pyridiniums substituted in the 4-position with electron withdrawing groups conjugated to the ring behaved like MV. These compounds showed reversible reduction at similar potentials and had Stern-Volmer (S-V) constants in the same range.

Alkyl pyridinium surfactants have been widely studied as fluorescence quenchers. Fluorophores that have been successfully quenched include polycyclic aromatic hydrocarbons (Pandey et al. 1999 *Talanta* 48:1103-1110; Palit et al. 1997 *Chem Phys Lett* 269:286-292; Wadek and Tucker 2000 *Talanta* 53:571-578; Mao et al. 2003 *J Sep Sci* 26:1643-1649), aminofluorene (Saha et al. 1999 *J Photochem Photobiol A* 121:191-198), and carbazole substituents on polymers (Yatsue et al. 1992 *J Phys Chem* 96:10125-10129).

Most studies were with simple N-alkyl pyridinium salts where the alkyl group was large enough to make the salt surface active. The polymer study was carried out with para-substituted N-alkyl pyridiniums, including derivatives of 4-acetyl pyridine, methyl isonicotinate, and isonicotinamide. In other studies with ring substituted pyridiniums, bis-picolinium salts with N,N'-alkylene bridging groups were used to quench the fluorescence of naphthols. The quenching efficiency of the bis compounds was substantially higher than that of a mono-picolinium control; and was highest for the compound with a methylene linker. (Panda et al. 1998 *J Photochem Photobio A* 113:73-80).

SUMMARY OF THE INVENTION

A terpyridinium quencher having the structure (T-1) below is disclosed in accordance with preferred embodiments of the present invention.

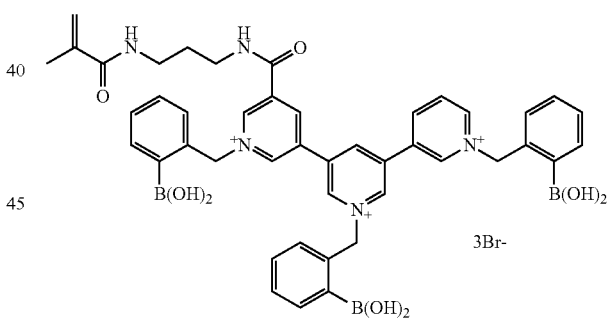

A method of making T-1 is disclosed in accordance with another embodiment of the present invention comprising the steps of:

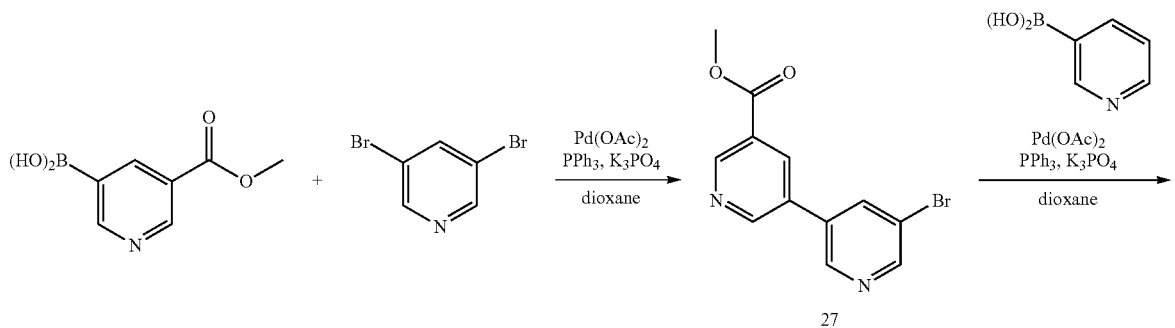

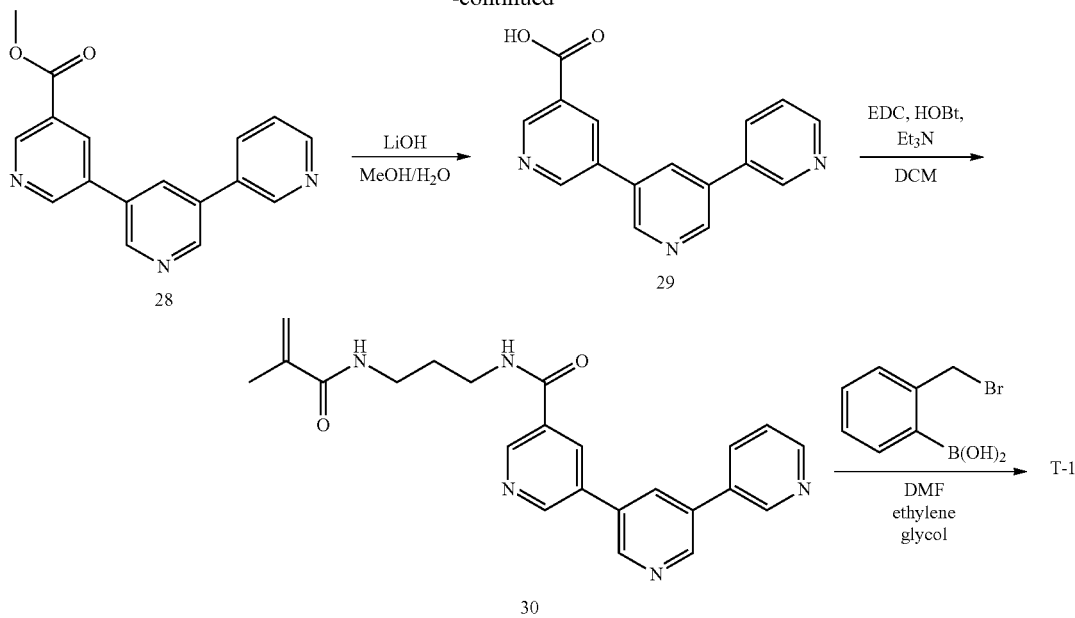
A terpyridinium quencher having the structure (T-2) below is disclosed in accordance with preferred embodiments of the present invention.
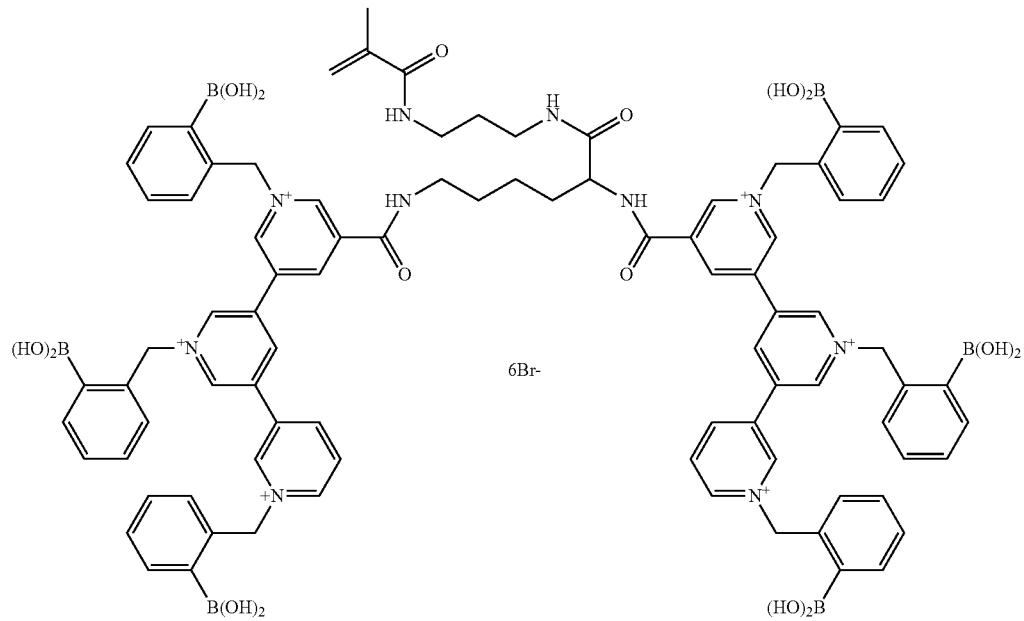
A method of making T-2 is disclosed in accordance with another embodiment of the present invention comprising the steps of:
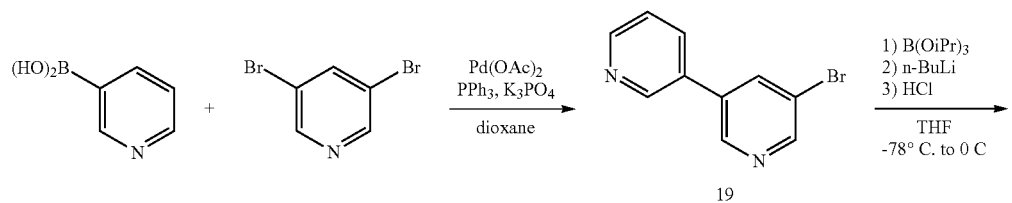

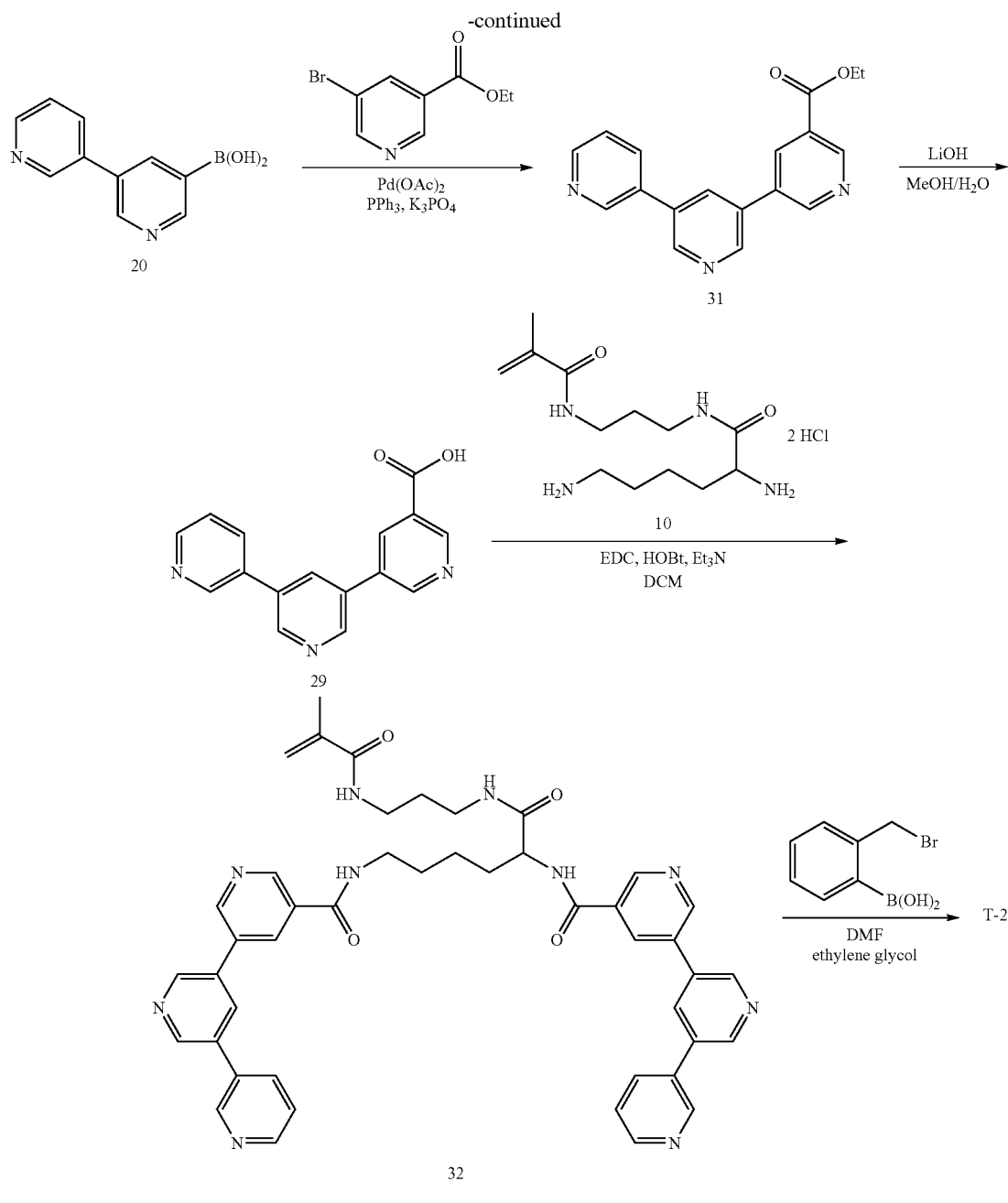

Pyridinium quenchers having generic structures as shown below are disclosed in accordance with preferred embodiments of the present invention.

A. Reactive Compound:

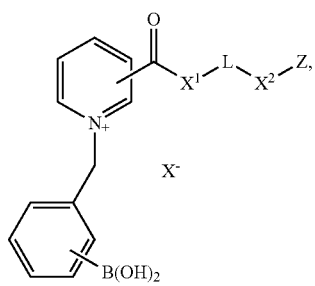

wherein:
X— is a counterion;
$X^1$ is —O— or —NH—;
$X^2$ is —O— or —NH—;
L is a divalent linking group selected from a direct bond or, a lower alkylene having 1 to 8 carbon atoms, optionally terminated with or interrupted by one or more divalent connecting groups selected from sulfonamide (—$SO_2$NH—), amide —(C=O)N—, ester —(C=O)—O—, ether —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms);
Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

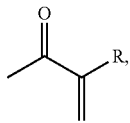

wherein R is H or CH$_3$;

is substituted on the pyridinium ring in the meta or para position; and

—B(OH)$_2$ may be in the ortho, meta or para position.

B. Non-Reactive Compound:

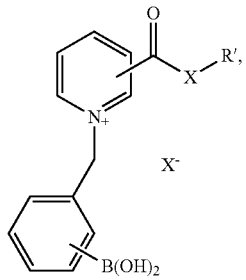

wherein

X is —O— or —NH—; and

R' is an alkyl, optionally including —O— units in the carbon chain and terminated with —OH or —OCH$_3$.

A pyridinium quencher having the structure (P-1) below is disclosed in accordance with preferred embodiments of the present invention.

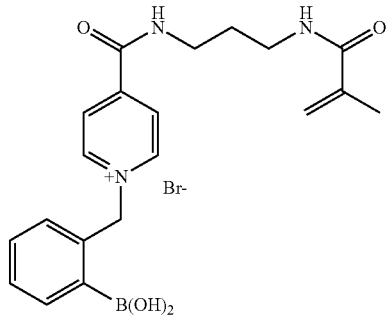

P-1

A method of making P-1 is disclosed in accordance with another embodiment of the present invention comprising the steps of:

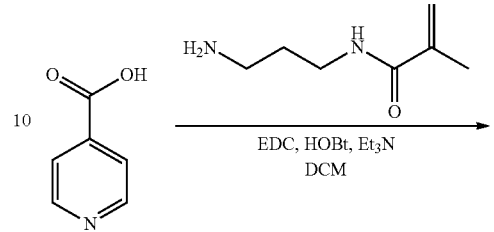

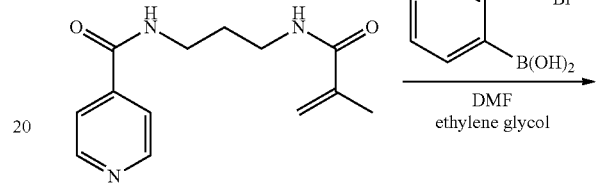

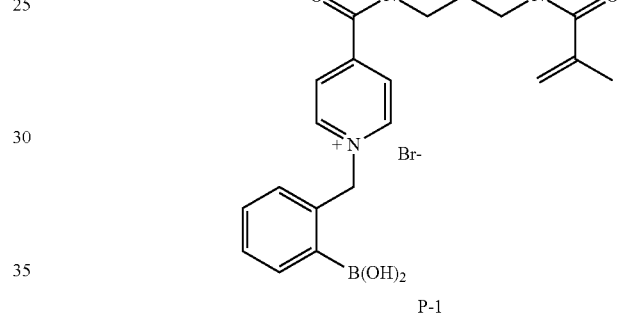

P-1

A pyridinium quencher having the generic structure below is disclosed in accordance with preferred embodiments of the present invention.

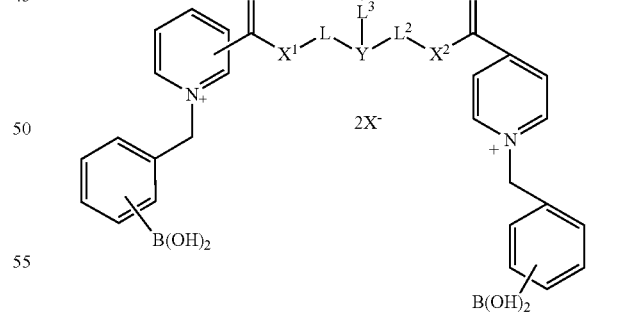

wherein

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

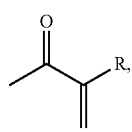

wherein R is H or CH$_3$;
Y is a trivalent connecting group selected from

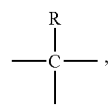

where R is H or a lower alkyl, and

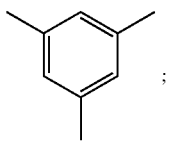

X$^1$ and X$^2$ are —O— or —NH—; and
L$^1$, L$^2$, and L$^3$ are selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof.

A pyridinium quencher having the structure (P-2) below is disclosed in accordance with preferred embodiments of the present invention.

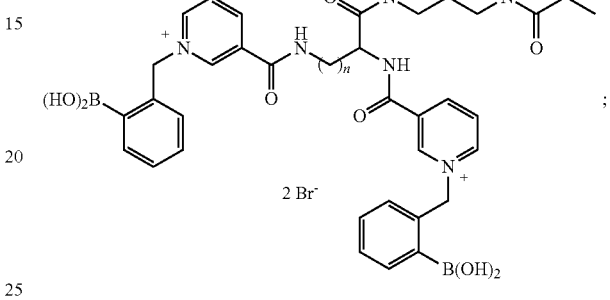

wherein n=1-10.

A method of making P-2 is disclosed in accordance with another embodiment of the present invention comprising the steps of:

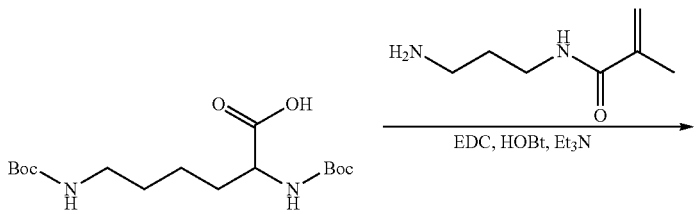

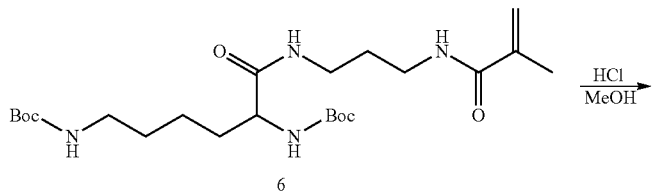

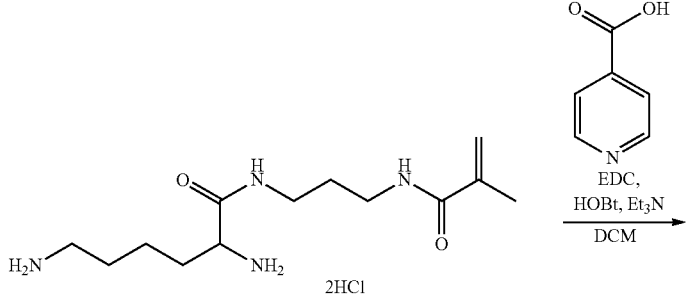

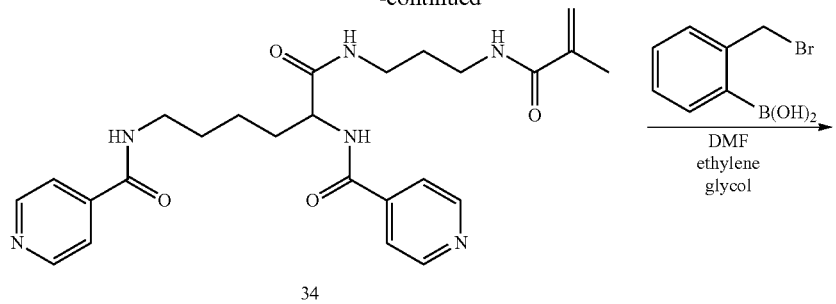

34

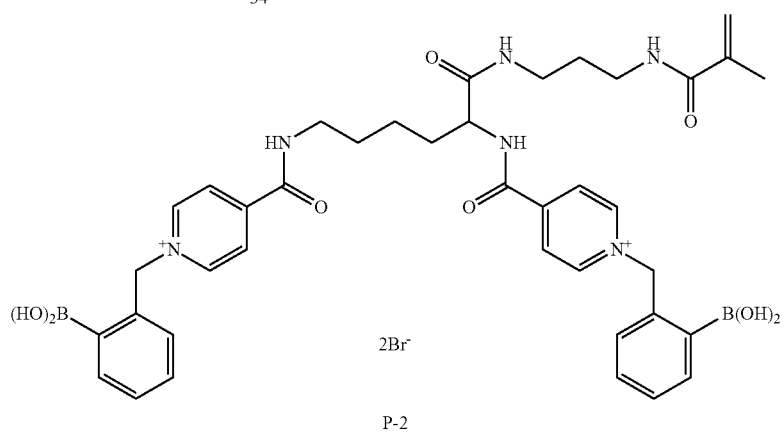

P-2

Another pyridinium boronic acid quencher having the generic structure below is disclosed in accordance with preferred embodiments of the present invention.

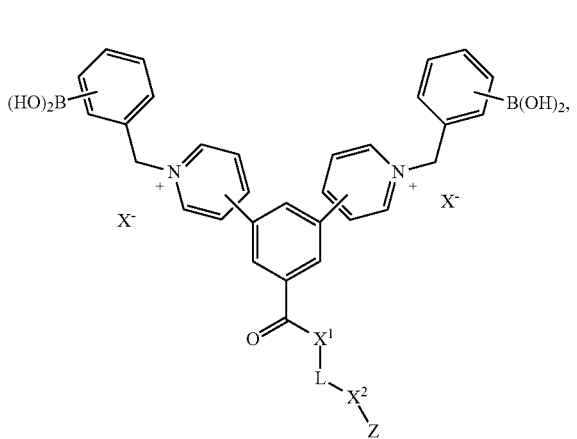

wherein
X⁻ is a counterion;
X¹ is —O— or —NH—;
X² is —O— or —NH—;
L is a divalent linking selected from a direct bond or, a lower alkylene having 1 to 8 carbon atoms, optionally terminated with or interrupted by one or more divalent connecting groups selected from sulfonamide (—SO₂NH—), amide —(C=O)N—, ester —(C=O)—O—, ether —O—, sulfide —S—, sulfone (—SO₂—), phenylene —C₆H₄—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof;

Z is a reactive group selected from a coupling group or an olefinically unsaturated group, or Z is

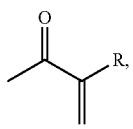

wherein R is H or CH₃;
the bond from the central benzene ring is to the ortho, meta or para position on the adjacent pyridinium rings; and
—B(OH)₂ may be in the ortho, meta or para position.
A specific pyridinium boronic acid quencher, termed P-3, having the structure below is disclosed in accordance with preferred embodiments of the present invention.

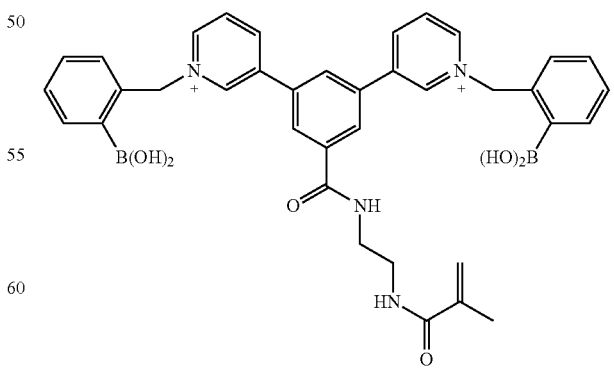

A method of making P-3 is disclosed in accordance with another embodiment of the present invention comprising the steps of:

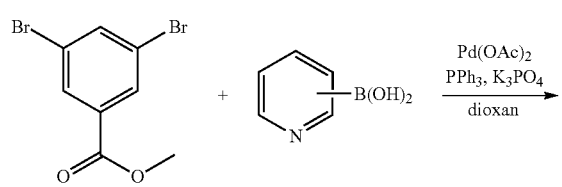

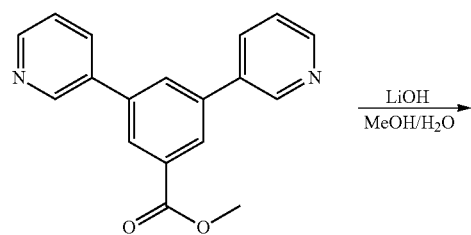

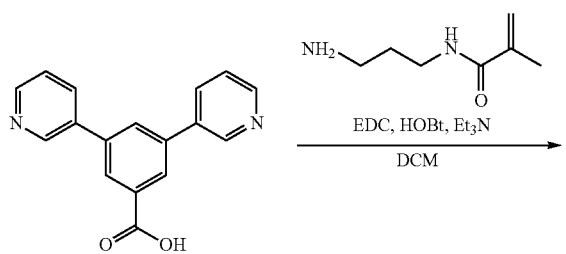

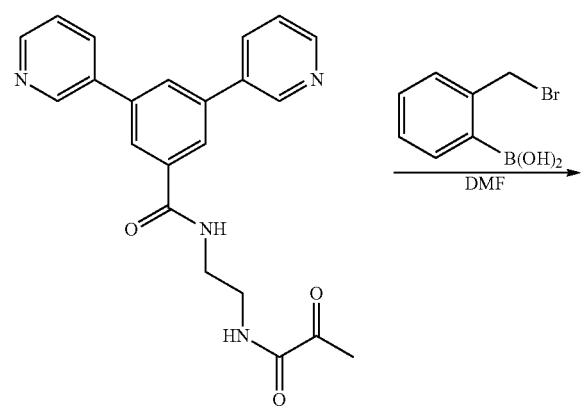

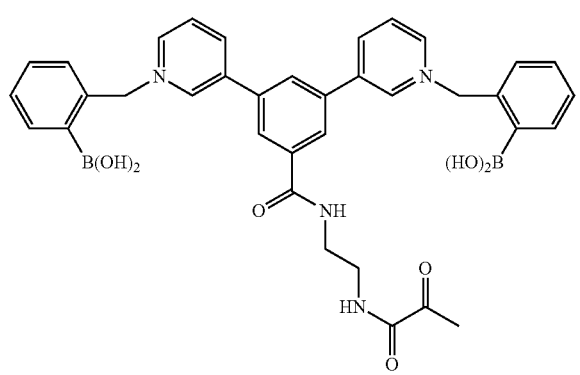

Another pyridinium boronic acid quencher having the generic structure below is disclosed in accordance with preferred embodiments of the present invention.

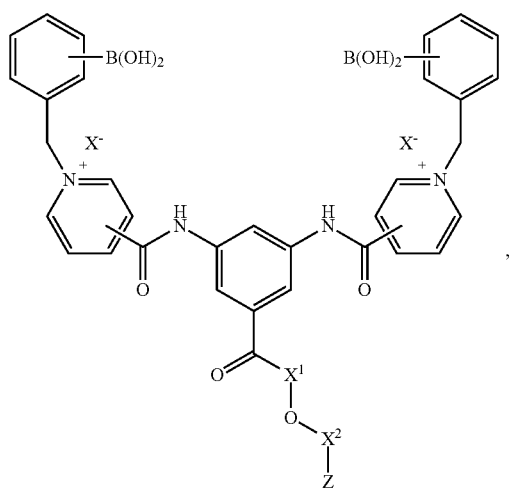

wherein
X⁻ is a counterion;
$X^1$ is —O— or —NH—;
$X^2$ is —O— or —NH—;
L is a divalent linking selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof;
Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

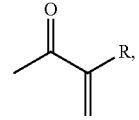

wherein R is H or CH$_3$;
the ambiguously depicted bonds are in the ortho, meta or para position; and
—B(OH)$_2$ may be in the ortho, meta or para position.

Another pyridinium boronic acid quencher, termed P-4, having the structure below is disclosed in accordance with preferred embodiments of the present invention.

P-4

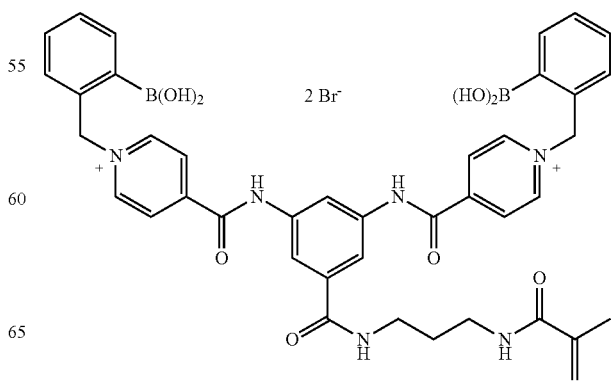

A method of making P-4 is disclosed in accordance with another embodiment of the present invention comprising the steps of:

component, e.g., a polymer matrix or a semipermeable membrane, that provides a means for immobilizing the dye and quencher.

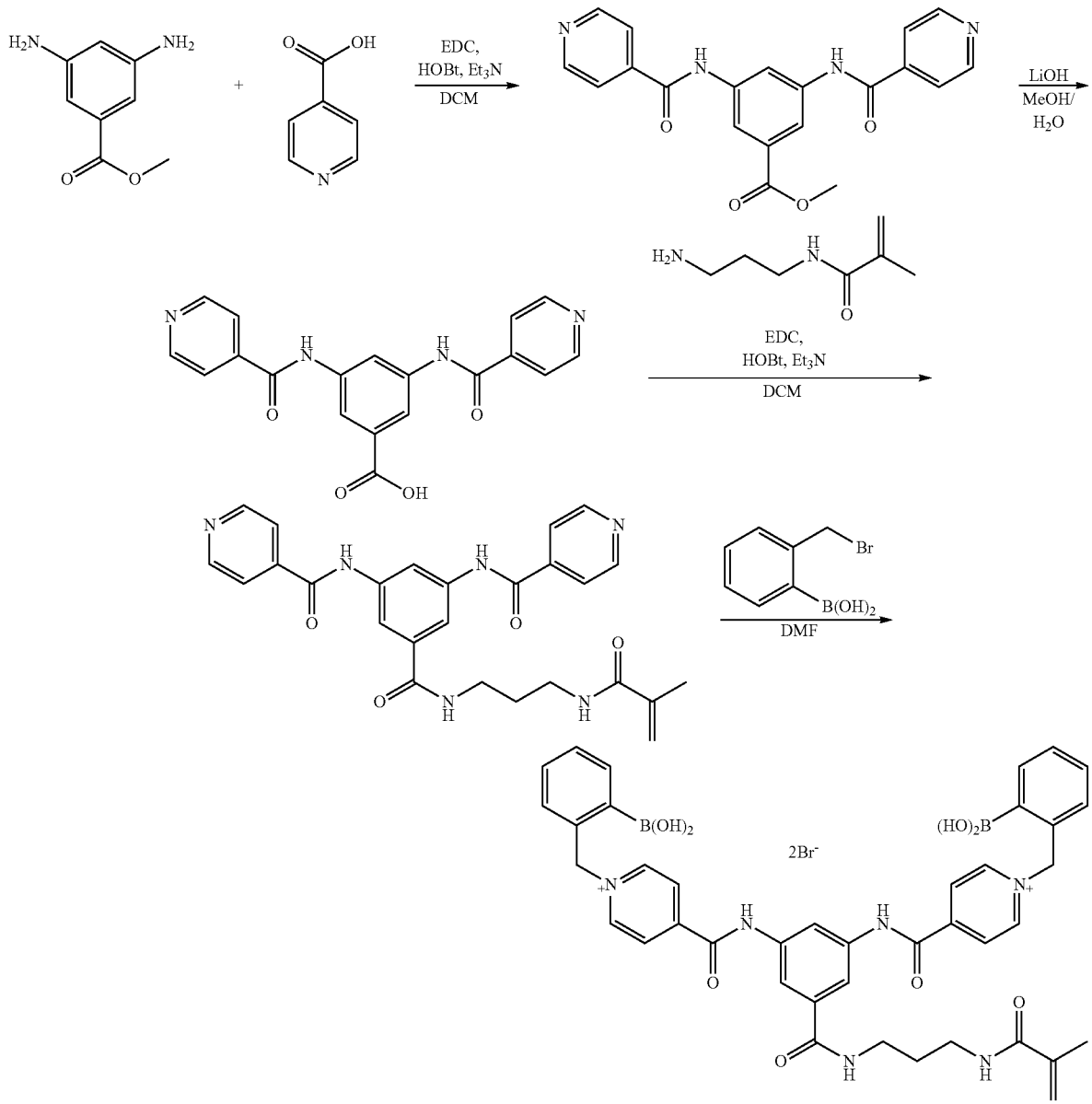

In one embodiment, an analyte sensor is disclosed comprising a fluorophore configured to absorb light at a first wavelength and emit light at a second wavelength and a quencher configured to modify the light emitted by the fluorophore by an amount related to the analyte concentration, wherein the quencher comprises a boronic acid-substituted pyridinium. In preferred embodiments, the quencher is selected from the group consisting of P1, P2, P3 and P4.

A glucose sensor is disclosed in accordance with another embodiment of the present invention, comprising any one or more analyte-binding moieties selected from the group consisting of T-1, T-2, P-1, P-2, P-3 and P-4; a fluorescent dye, e.g., HPTS-triCys-MA; and optionally an analyte permeable

BRIEF DESCRIPTION OF THE DRAWINGS

FIG. 1 illustrates the glucose response of a sensor comprising quencher P-1 and dye HPTS-triCys-MA immobilized within a hydrogel at the tip of an optical fiber. The detection chemistry was excited at 470 nm and fluorescence was measured between 520-700 nm in the presence of increasing concentrations of glucose.

DETAILED DESCRIPTION OF THE PREFERRED EMBODIMENT

Fluorescent dyes and analyte-binding moieties that modulate fluorescence upon binding analyte are known and have been used in indicator systems for analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 10/456,895, 11/296,898, 11/671,880, 60/833,081, 60/888,477, and 60/888,475; each of which is incorporated herein in its entirety by reference thereto.

Although Applicants do not intend to be bound by the proposed mechanism of action, one mechanism that may be employed in some of the preferred indicator systems described in the above-referenced co-pending US patent applications includes inter alia the formation of a ground state complex between the analyte-binding moiety and the fluorescent dye. As a result of the formation of the complex, the fluorescence may be quenched. When the boronic acid group on the preferred analyte-binding moiety reacts with a polyhydroxyl-substituted organic molecule such as glucose, the boron becomes negatively charged. This weakens the complex, resulting in dissociation, and an increase in fluorescence that is related to glucose concentration.

The indicator systems of the present invention for the detection of polyhydroxyl-substituted organic molecules (e.g., sugars) comprise a novel class of pyridinium salts functionalized with boronic acids as the analyte binding moieties. In embodiments of the present invention, the analyte-binding pyridinium quenchers exhibit one or more of the following characteristics. They are: 1) compatible with aqueous media; 2) substituted with boronic acid groups; 3) inherently positively charged, preferably with at least one cationic group per boronic acid; and 4) amenable to immobilization. The analyte-binding quenchers are hypothesized to be good electron acceptors and the electron transfer process is reversible.

As used herein, "boronic acid" refers to a structure —B(OH)$_2$. It is recognized by those skilled in the art that a boronic acid may be present as a boronate ester at various stages in the synthesis of the quenchers of this invention. Boronic acid is meant to include such esters.

"Fluorophore" refers to a substance that when illuminated by light at a particular wavelength emits light at a longer wavelength; i.e., it fluoresces. Fluorophores include organic dyes, organometallic compounds, metal chelates, fluorescent conjugated polymers, quantum dots or nanoparticles and combinations of the above. Fluorophores may be discrete moieties or substituents attached to a polymer. "Fluorescent dye" or "dye" is selected from a discrete compound or a reactive intermediate which is convertible to a second discrete compound, or to a polymerizable compound.

"Linking group", also termed "L", refers to divalent moieties that covalently connect the sensing moiety to the polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like.

"Quencher" refers to a compound that reduces the emission of a fluorophore when in its presence.

"Pyridinium" refers to a pyridine substituted on the nitrogen to form a positively charged onium salt, optionally substituted at other positions on the pyridine ring.

Pyridinium Quenchers

Pyridinium salts functionalized with boronic acids for use as analyte-binding quenchers have been synthesized. In accordance with preferred embodiments, useful pyridiniums are substituted with carbonyl groups and are structurally configured and functionally adapted to bind polyhydroxyl-substituted organic molecules (e.g., sugars) and may be used in chemical indicator systems of glucose sensors as alternatives to viologen-boronic acid adducts, such as 3,3'-oBBV or derivatives thereof, described e.g., in co-pending U.S. patent application Ser. Nos. 11/296,898 and 11/671,880.

The moiety that provides recognition of polyhydroxyl-substituted organic molecules (e.g., glucose) is an aromatic boronic acid. The boronic acid is either attached via a linker group or covalently bonded to a conjugated nitrogen-containing heterocyclic aromatic structure. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the fluorophore by the pyridinium resulting in an increase in fluorescence dependent on glucose concentration.

A generic structure of a reactive compound is shown below:

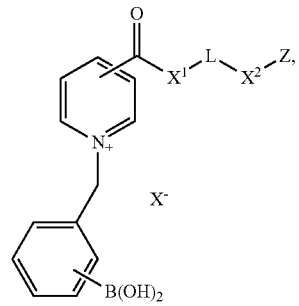

wherein:
X— is a counterion;
X$^1$ is —O— or —NH—;
X$^2$ is —O— or —NH—;
L is a divalent linking selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof;
Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

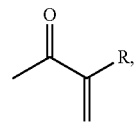

wherein R is H or CH$_3$;

is substituted on the pyridinium ring in the meta or para position, and

—B(OH)$_2$ may be in the ortho, meta or para position.

A generic structure of a non-reactive compound is shown below

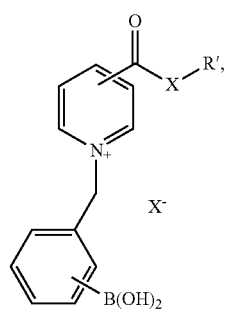

wherein

X is —O— or —NH—; and

R' is an alkyl, optionally including —O— units in the carbon chain and terminated with —OH or —OCH$_3$.

A pyridinium quencher having the structure (P-1) below is disclosed in accordance with preferred embodiments of the present invention.

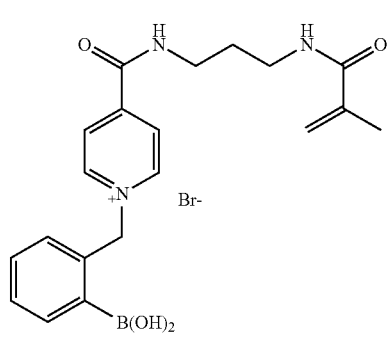

P-1

A method of making P-1 is disclosed in accordance with another embodiment of the present invention comprising the steps of:

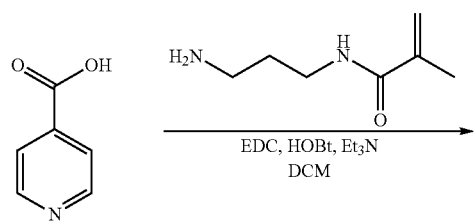

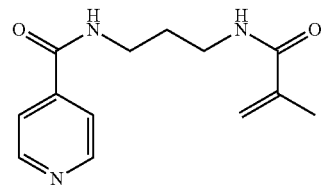

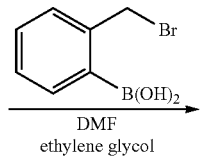

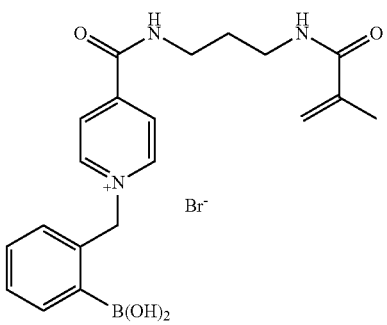

P-1

A pyridinium quencher having the generic structure below is disclosed in accordance with preferred embodiments of the present invention.

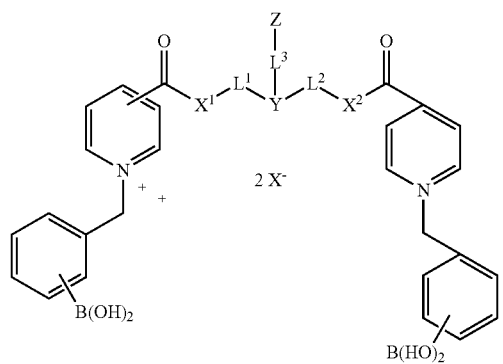

wherein

Z is a reactive group as previously defined;

Y is a trivalent connecting group selected from

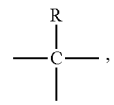

where R is H or a lower alkyl, and

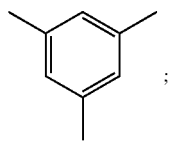
;

$X^1$ and $X^2$ are —O— or —NH—; and $L^1$, $L^2$, and $L^3$ are selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof.

A pyridinium quencher having the structure (P-2) below is disclosed in accordance with preferred embodiments of the present invention.

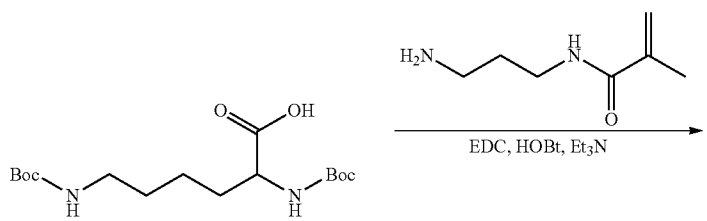
;

wherein n=1-10.

One purpose of the bridging group between the boronic acid functionalized pyridinium groups is to allow the two boronic acids to bind cooperatively to one glucose molecule. The inventors hypothesize that this may result in enhanced glucose selectivity. Rather than being a simple carbon chain (as illustrated, wherein n=1-10), the bridging group could also include other chemical linkages, such as e.g., ethylene oxide segments. P-2 is representative of a family of poly benzylboronic acid pyridinium salts wherein the pyridinium rings are connected by a bridging group attached at the meta- and para-positions through a carbonyl substituent.

A method of making P-2 is disclosed in accordance with another embodiment of the present invention comprising the steps of:

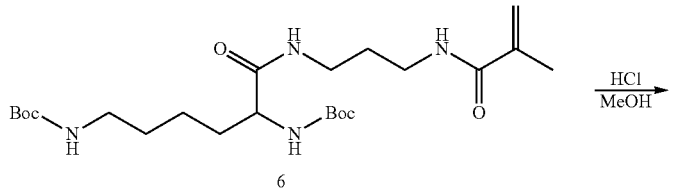

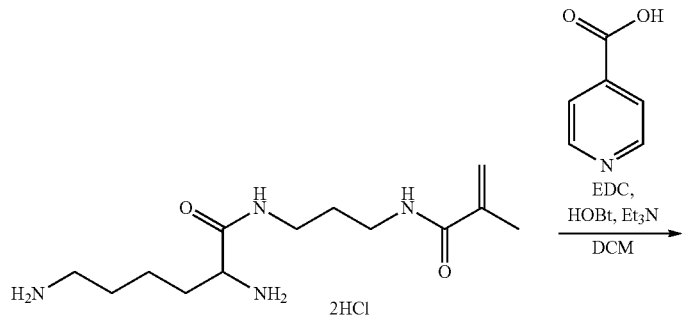

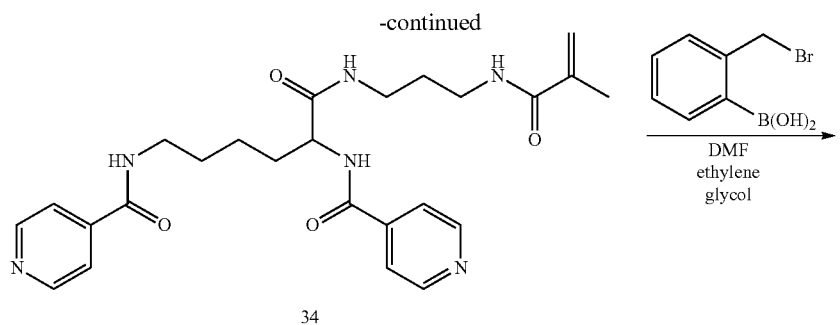

34

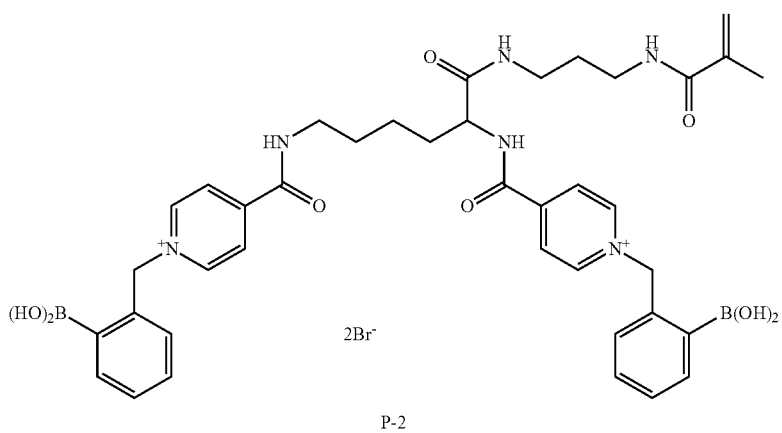

P-2

Another pyridinium boronic acid quencher having the generic structure below is disclosed in accordance with preferred embodiments of the present invention.

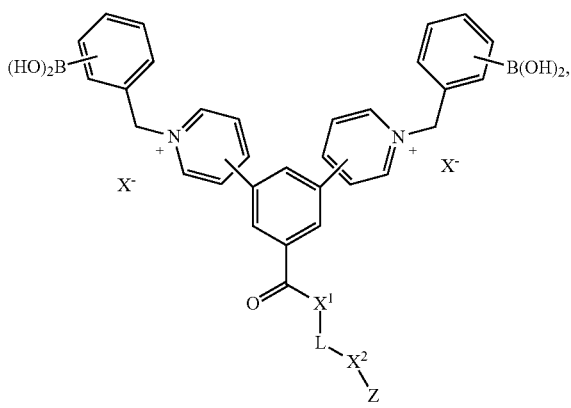

wherein
X⁻ is a counterion;
X¹ is —O— or —NH—;
X² is —O— or —NH—;
L is a divalent linking selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH (C═O)—O—, urea —NH(C═O)NH—, thiourea —NH(C═S)—NH—, amide —(C═O)NH—, amine —NR— (where R is defined as alkyl having 1 to 6 carbon atoms) or combinations thereof;

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

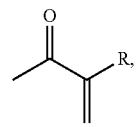

wherein R is H or CH$_3$;
the bond from the central benzene ring is to the ortho, meta or para position on the adjacent pyridinium rings; and
—B(OH)$_2$ may be in the ortho, meta or para position.

A specific pyridinium boronic acid quencher, termed P-3, having the structure below is disclosed in accordance with preferred embodiments of the present invention.

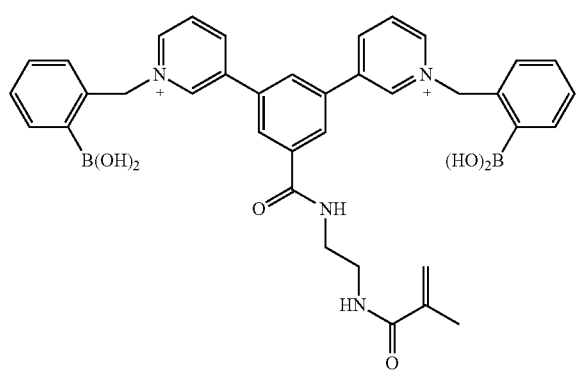

A method of making P-3 is disclosed in accordance with another embodiment of the present invention comprising the steps of:

Another pyridinium boronic acid quencher having the generic structure below is disclosed in accordance with preferred embodiments of the present invention.

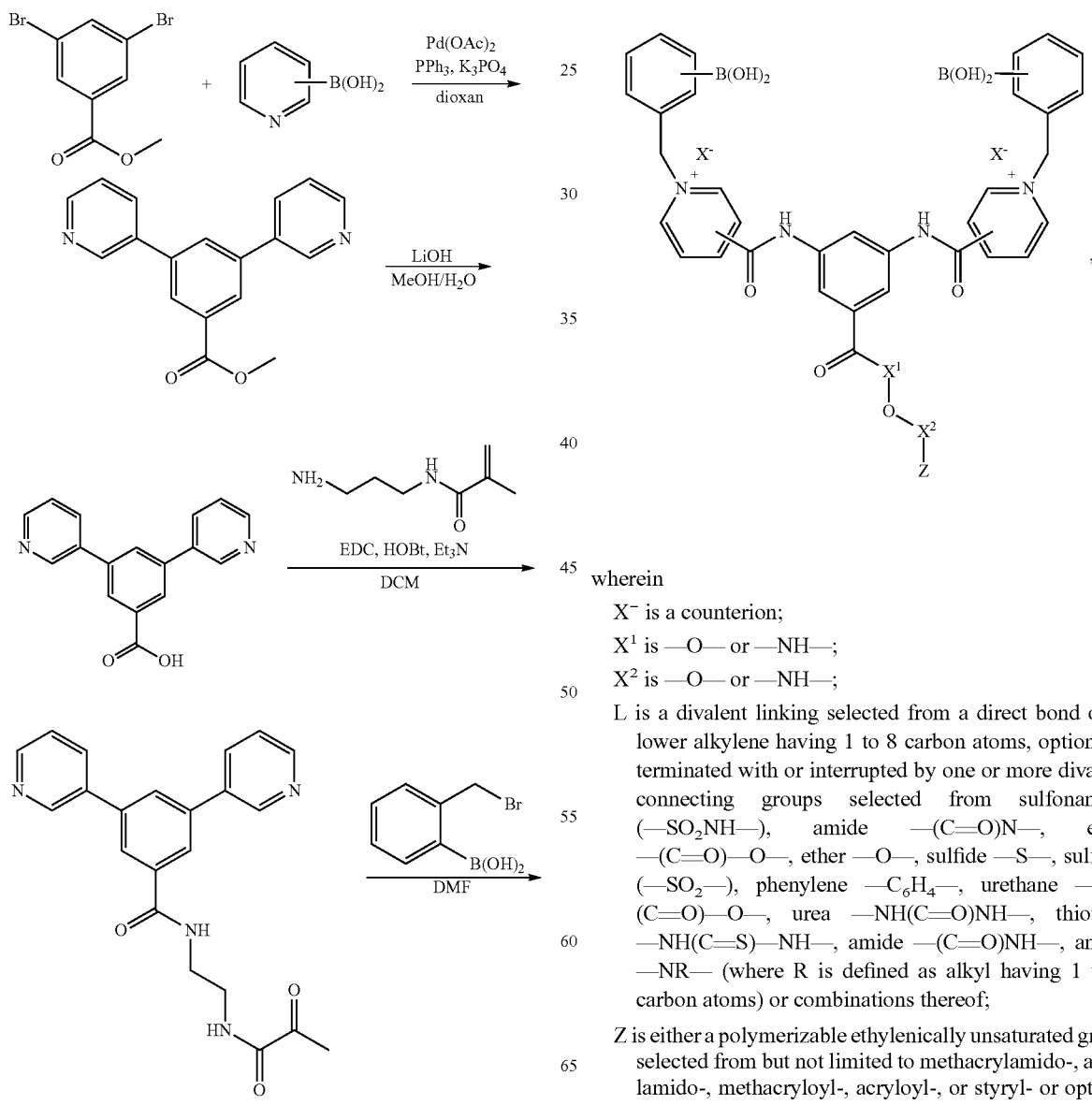

wherein

X⁻ is a counterion;

$X^1$ is —O— or —NH—;

$X^2$ is —O— or —NH—;

L is a divalent linking selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH(C═O)—O—, urea —NH(C═O)NH—, thiourea —NH(C═S)—NH—, amide —(C═O)NH—, amine —NR— (where R is defined as alkyl having 1 to 6 carbon atoms) or combinations thereof;

Z is either a polymerizable ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

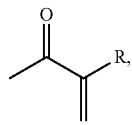

wherein R is H or CH$_3$;

the ambiguously depicted bonds are in the ortho, meta or para position; and

—B(OH)$_2$ may be in the ortho, meta or para position.

Another pyridinium boronic acid quencher, termed P-4, having the structure below is disclosed in accordance with preferred embodiments of the present invention.

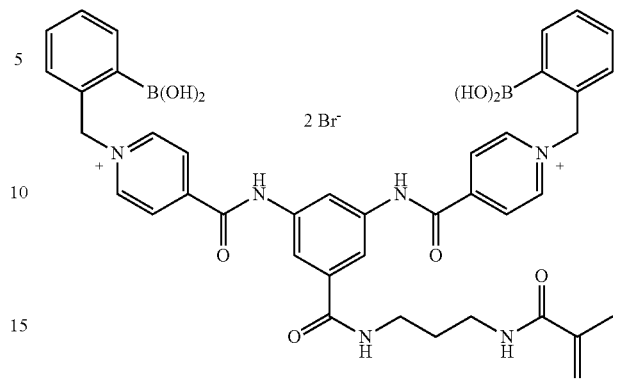

A method of making P-4 is disclosed in accordance with another embodiment of the present invention comprising the steps of:

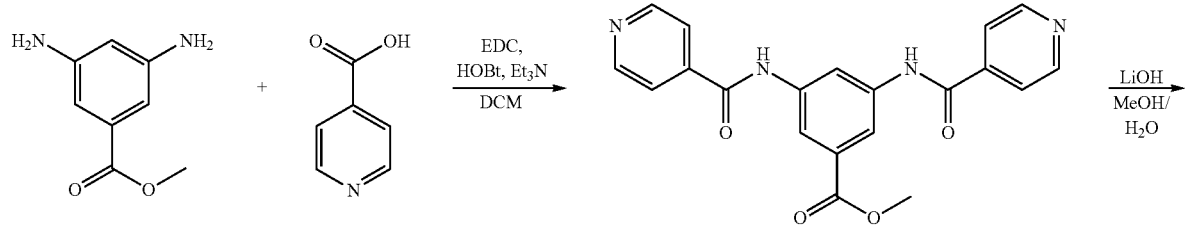

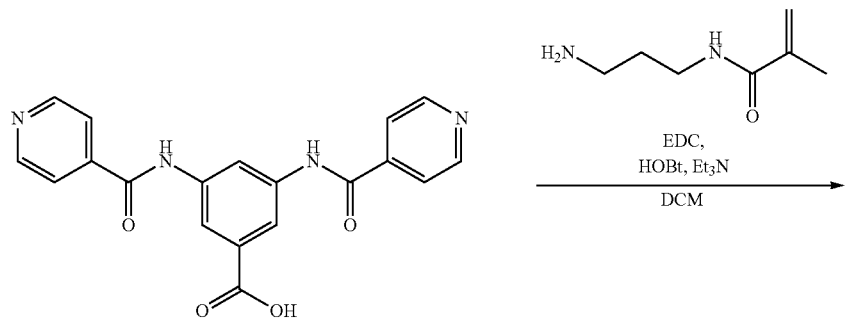

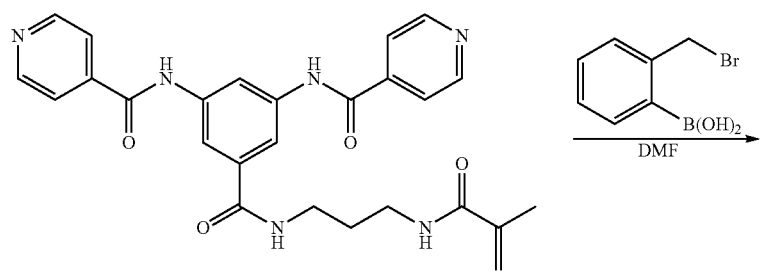

-continued

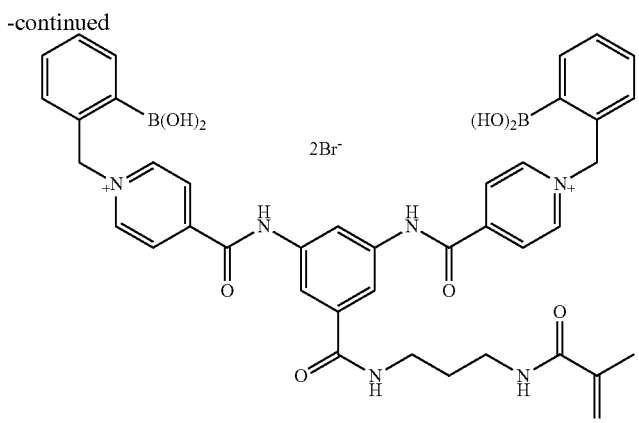

Some pyridinium quenchers disclosed herein encompass monovalent structures with a single benzyl boronic acid group. P-1 is one such representative of this new class of polymerizable, benzyl boronic acid pyridinium salts. It is a simple molecule that is easy to make from readily available intermediates and it performs like viologen-based hydrogels.

Other embodiments of pyridinium quenchers, termed polypyridinium quenchers have three or more benzyl boronic acid groups (e.g., T-1 and T-2). These compounds differ from both monovalent pyridinium variants such as P-1 and from viologens, which comprise two benzyl boronic acid groups. T-1 and T-2 are fully N-alkylated polypyridines, wherein the pyridine rings are directly coupled (i.e., no linking group between rings). They can also be classified as extended conjugation viologens (i.e., two pyridinium rings connected by a conjugated bridging moiety). The T-2 polypyridinium quencher comprises a trifunctional moiety that links to a reactive group and two terpyridinium groups.

As disclosed herein, P2, P3 and P4 are bis-pyridiniums. Boronic acid substituted polypyridiniums are another class of preferred quenchers, wherein there are more than two rings coupled together. The term "polypyridinium" includes: a discrete compound comprised of three or more pyridinium groups covalently bonded together by a linking group, a polymer comprised of pyridinium repeat units in the chain, a polymer with pyridinium groups pendant to the chain, a dendrimer comprised of pyridinium units, preferably including pyridinium terminal groups, an oligomer comprised of pyridinium units, preferably including pyridinium endgroups, and combinations thereof.

In some embodiments, the quenchers disclosed herein are substituted with at least two boronic acid groups and are water-soluble or dispersible polymers or hydrogels comprised of polypyridinium boronic acids. Alternatively, the polypyridinium boronic acid is directly bonded to an inert substrate. Quencher precursors comprised of polypyridinium boronic acids include low molecular weight polypyridinium boronic acids further substituted with polymerizable groups or coupling groups.

Some of the structures disclosed herein are quencher precursors (i.e., monomers) used to make the sensing polymers. It would not be practical to use the monomers as quenchers for in vitro applications due to their reactivity. On the other hand, non-polymerizable versions can be made that are useful for in vitro applications. These embodiments comprise a non-polymerizable group (e.g., the methacrylamido group can be replaced with a solubilizing group such as a PEG substituent).

In some embodiments, the monovalent- or polypyridinium-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the monovalent- or polypyridinium-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix by a linker as described herein. The quencher may be linked to a water-insoluble polymer matrix at one or two sites in some embodiments.

Analyte Sensors

The chemical indicator systems used in accordance with preferred embodiments of the present invention comprise a fluorophore operably coupled to an analyte binding moiety, wherein analyte binding causes an apparent optical change in the fluorophore concentration (e.g., emission intensity). It is further desired that the fluorophore has different acid and base forms that exhibit a detectable difference in spectral properties such that ratiometric pH sensing may be enabled; see e.g., co-pending U.S. patent application Ser. No. 11/671,880. For example, a glucose binding moiety, e.g., P-1 that is operably coupled to a fluorescent dye, such as HPTS-triCysMA, will quench the emission intensity of the fluorescent dye, wherein the extent of quenching is reduced upon glucose binding resulting in an increase in emission intensity related to glucose concentration. P-1 has at least one boronic acid per pyridinium whereas other pyridinium quenchers may have multiple pyridinium rings, some of which are not substituted with boronic acid groups.

In further preferred embodiments, the indicator systems also comprise a means for immobilizing the sensing moieties (e.g., dye-quencher) such that they remain physically close enough to one another to react (quenching). Where in vivo sensing is desired, such immobilizing means are preferably insoluble in an aqueous environment (e.g., intravascular), permeable to the target analytes, and impermeable to the sensing moieties. Typically, the immobilizing means comprises a water-insoluble organic polymer matrix. For example, the dye and quencher may be effectively immobilized within a DMAA (N,N-dimethylacrylamide) hydrogel matrix, which allows glucose sensing in vivo.

Some exemplary fluorophores and immobilizing means are set forth in greater detail below. In some embodiments, useful dyes include pyranine derivatives (e.g. hydroxypyrene trisulfonamide derivatives and the like). In other embodiments, the dye may be one of the polymeric derivatives of hydroxypyrene trisulfonic acid.

In one preferred embodiment, the fluorescent dye may be HPTS-TriCys-MA:

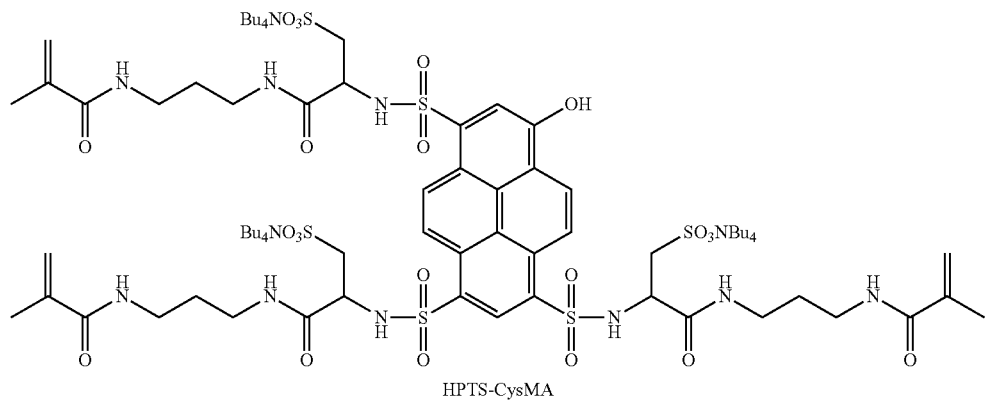

HPTS-CysMA

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides $NBu_4^+$ may be used, including positively charged metals, e.g., $Na^+$. In other variations, the sulfonic acid groups may be replaced with e.g., phosphoric, carboxylic, etc. functional groups.

In some embodiments, for use in vitro not involving a moving stream, the sensing components are used as individual (discrete) components. The fluorophore and quencher are mixed together in liquid solution, analyte is added, the change in fluorescence intensity is measured, and the components are discarded. Polymeric matrices that can be used to trap the sensing components to prevent leaching need not be present. Optionally, the sensing components are immobilized which allows their use to measure analytes in a moving stream.

Applications in vivo

For in vivo applications, the analyte sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably, the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N, N', N''-tris(methacrylamidopropylsulfonamide), the quencher moiety is derived from an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl)bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and polymerizing the mixture. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorescent dye and quencher moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

EXAMPLE 1

Synthesis of T-1

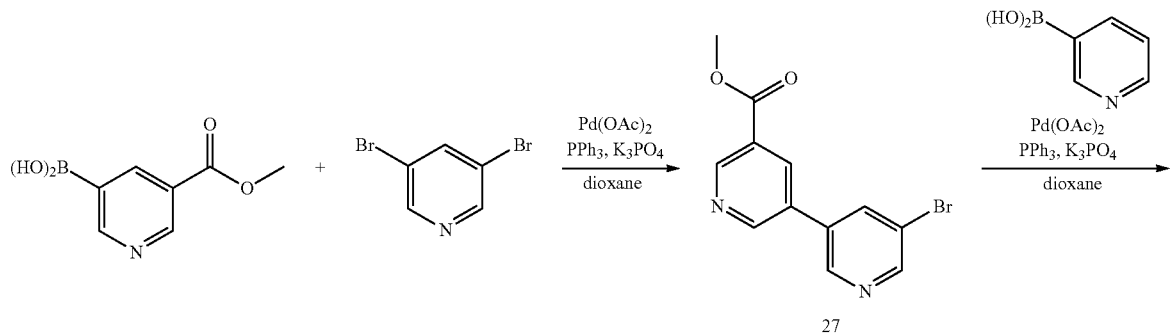

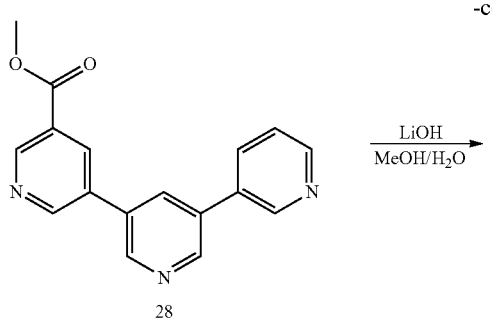

28

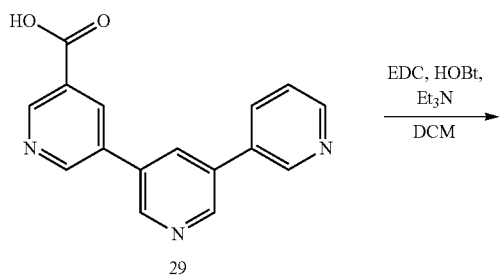

29

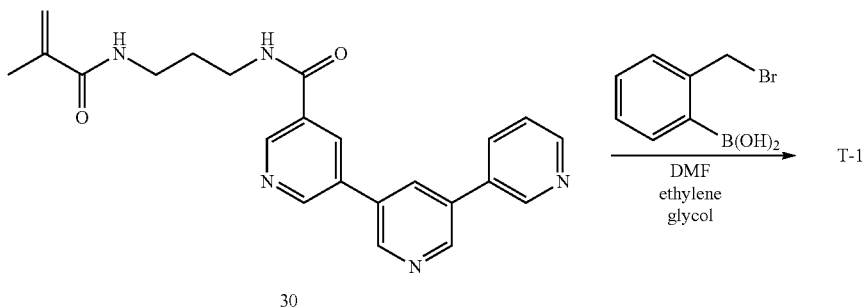

30

Compound 27—To a solution of 3,5-dibromopyridine (0.47 g, 2.0 mmol) in anhydrous 1,4-dioxane (15 mL), was added an aqueous solution of $K_3PO_4$ (2 M, 3 mL), followed by $PPh_3$ (0.21 g, 0.8 mmol) and $Pd(OAc)_2$ (0.05 g, 0.2 mmol). After stirring for 5 min., [5-(methoxycarbonyl)pyridin-3-yl] boronic acid (0.9 g, 5 mmol) was added, and the reaction was refluxed for 2 h. while a gentle and steady stream of argon was bubbled through the solution. After cooling to room temperature, water (10 mL) was added, and the reaction was extracted with EtOAc (50 mL). The organic layer was separated, dried over $MgSO_4$, concentrated in vacuo, and purified by flash column chromatography (100% $CHCl_3$) to give compound 27 (0.3 g, 51%). TLC: $R_f$=0.49 (2% MeOH/$CHCl_3$). $^1$H NMR ($CDCl_3$, 500 MHz) δ 4.01 (s, 3H), 8.08 (t, J=2.1 Hz, 1H), 8.49 (t, J=2.1 Hz, 1H), 8.77 (d, J=2.2 Hz, 1H), 8.80 (d, J=2.0 Hz, 1H), 9.0 (d, J=2.3 Hz, 1H), 9.28 (d, J=2.0 Hz, 1H).

Compound 28—To a suspension of compound 27 (0.3 g, 1.0 mmol) and 3-pyridineboronic acid (0.14 g, 1.1 mmol) in anhydrous 1,4-dioxane (5 mL), was added $PPh_3$ (0.05 g, 0.2 mmol) and $Pd(OAc)_2$ (0.01 g, 0.05 mmol) followed by an aqueous solution of $K_3PO_4$ (2 M, 1.1 mL). The reaction was refluxed for 1.5 h. while a gentle and steady stream of argon was bubbled through the solution. After cooling to room temperature, EtOAc (10 mL) was added, and the organic layer was washed with dilute $NaHCO_3$ (5 mL), brine (5 mL), dried over $MgSO_4$, concentrated in vacuo, and purified by flash column chromatography (2%–20% methanol in DCM) to give compound 28 (0.24 g, 83%). $^1$H NMR ($CDCl_3$, 500 MHz) δ 4.02 (s, 3H), 7.48 (dd, J=8.1, 4.5 Hz, 1H), 7.97 (dt, J=7.9, 1.9 Hz, 1H), 8.10 (t, J=2.2 Hz, 1H), 8.57 (t, J=2.1 Hz, 1H), 8.72 (dd, J=4.8, 4.2 Hz, 1H), 8.93 (m, 3H), 9.08 (d, J=2.3 Hz, 1H), 9.30 (d, J=1.9 Hz, 1H).

Compound 29—To a suspension of compound 28 (0.24 g, 0.8 mmol) in THF (15 mL), MeOH (10 mL), and water (3 mL), was added LiOH (0.03 g, 1.4 mmol). After stirring for 15 min., the reaction became clear. The reaction was stirred for 18 h., and the volatiles were then evaporated. The remaining aqueous solution was diluted with NaOH (1 M, 20 mL), washed with DCM (10 mL), and acidified to pH 4 with $KHSO_4$ (1 M) to precipitate the product. The white solid was collected by filtration, washed with water and dried under vacuum 29 (0.21 g, 95%). $^1$H NMR (DMSO-d6, 500 MHz) δ 7.56 (ddd, J=7.9, 4.8, 0.8 Hz, 1H), 8.33 (ddd, J=7.9, 2.3, 1.7 Hz, 1H), 8.59 (t, J=2.2 Hz, 1H), 8.66 (dd, J=4.8, 1.6 Hz, 1H), 8.68 (t, J=2.2 Hz, 1H), 9.04 (dd, J=4.1, 2.2 Hz, 2H), 9.12 (m, 2H), 9.26 (d, J=2.3 Hz, 1H).

Compound 30—To a cooled (0° C.) suspension of compound 29 (0.21 g, 0.76 mmol) in dichloromethane (50 mL), was added N-(3-dimethylaminopropyl)-N'-ethylcarbodiimide hydrochloride (0.17 g, 0.9 mmol), 1-hydroxy-benzotriazole hydrate (0.12 g, 0.9 mmol), and triethylamine (0.15 mL, 1.1 mmol). After stirring for 30 min. at 0° C., N-(3-aminopropyl)methacrylamide hydrochloride (0.16 g, 0.9 mmol) and triethylamine (0.15 mL, 1.1 mmol) were added. The reaction was stirred for 18 h, then washed with saturated $NaHCO_3$ (3×25 mL). The DCM layer was dried with $MgSO_4$, reduced in volume in vacuo, and purified by flash column chromatography (2%-20% methanol in DCM) to give compound 30 (0.19 g, 62%) as a white solid. TLC: Rf=0.50 (10% MeOH/DCM on a plate treated with triethylamine). $^1$H NMR ($CDCl_3$, 500 MHz) δ 1.84 (p, J=6.0 Hz, 2H), 1.98 (s, 3H), 3.51 (q, J=6.5 Hz, 2H), 3.55 (q, J=6.1 Hz, 2H), 5.39 (s, 1H), 5.79 (s, 1H), 6.30 (t, 1H), 7.46 (dd, J=7.9, 4.9 Hz, 1H), 7.98 (ddd, J=7.9, 2.3, 1.7 Hz, 1H), 8.06 (t, 1H), 8.18 (t, J=2.2 Hz, 1H), 8.58 (t, J=2.2 Hz, 1H), 8.71 (dd, J=4.8, 1.5 Hz, 1H), 8.92 (d, J=2.1 Hz, 1H), 8.94 (d, J=1.9 Hz, 1H), 8.98 (d, J=2.2 Hz, 1H), 9.04 (d, J=2.2 Hz, 1H), 9.22 (d, J=2.1 Hz, 1H).

Compound T-1—2-Bromomethylphenyl boronic acid (0.6 g, 2.8 mmol) was added to a solution of compound 30 (0.19 g, 0.47 mmol) in DMF (3 mL) and ethylene glycol (0.16 mL, 2.8 mmol). The reaction was stirred at 55° C. for 72 h. Diethylether (20 mL) was added to separate the product as an oil. The solvent was decanted, and the remaining oil was sonicated in acetone until it became a pale yellow powder. The solid was collected by centrifugation, washed with acetone several times and dried under argon (0.29 g, 59%). $^1$H NMR (D2O, 500 MHz) δ 1.89 (p, J=6.8 Hz, 2H), 2.22 (s, 3H), 3.36 (t, J=6.8 Hz, 2H), 3.50 (t, J=6.6 Hz, 2H), 5.40 (s, 1H), 5.65 (s, 1H), 6.10 (s, 2H), 6.16 (s, 2H), 6.17 (s, 2H), 7.60 (m, 9H), 7.80 (m, 3H), 8.26 (dd, J=8.1, 6.3 Hz, 1H), 8.93 (d, J=8.5 Hz, 1H), 9.07 (t, J=6.2 Hz, 1H), 9.25 (m, 2H), 9.28 (t, J=1.6 Hz, 1H), 9.32 (d, J=5.3 Hz, 2H), 9.39 (s, 1H), 9.46 (s, 1H).

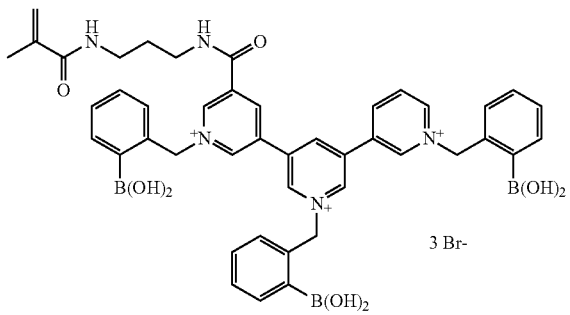

T-1

EXAMPLE 2

Synthesis of T-2

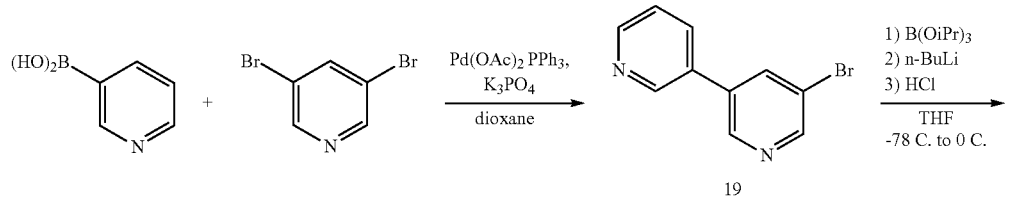

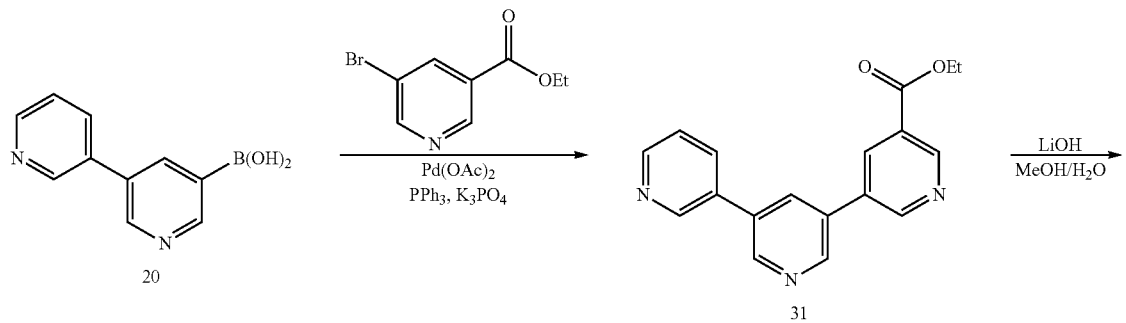

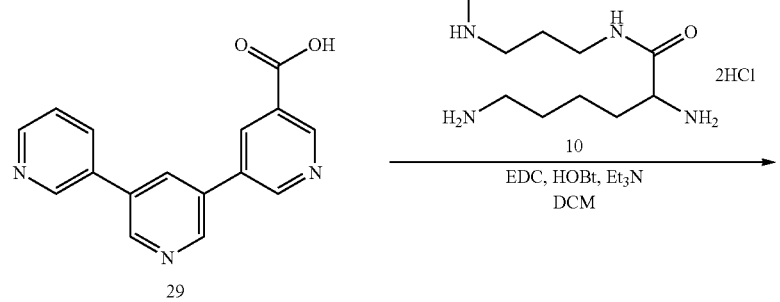

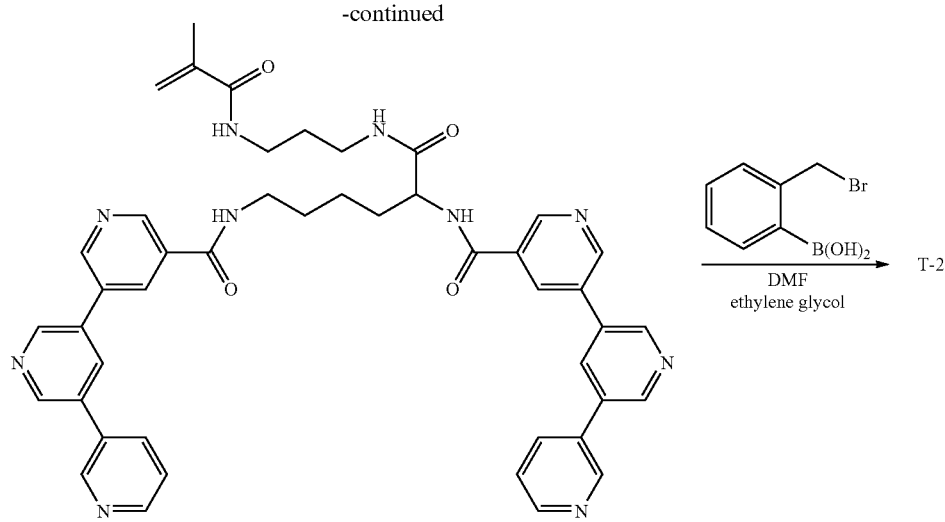

Compound 19—To a suspension of 3,5-dibromopyridine (2.1 g, 9.0 mmol) and 3-pyridineboronic acid (1.1 g, 9.0 mmol) in anhydrous 1,4-dioxane (40 mL), was added an aqueous solution of $K_3PO_4$ (2 M, 9 mL), followed by $PPh_3$ (0.5 g, 2.0 mmol) and $Pd(OAc)_2$ (0.11 g, 0.5 mmol). The reaction was refluxed for 2 h. while a gentle and steady stream of argon was bubbled through the solution. After cooling to room temperature, the aqueous layer was extracted with EtOAc (1×100 mL). The organic layer was washed with dilute $NaHCO_3$ (3×50 mL) and brine (1×50 mL), dried over $MgSO_4$, concentrated in vacuo, and purified by flash column chromatography (2%-20% methanol in DCM) to give compound 19 (1.3 g, 61%). TLC: $R_f$=0.63 (10% MeOH/DCM). $^1H$ NMR ($CD_3OD$, 500 MHz) δ 7.59 (ddd, J=8.0, 4.9, 0.8 Hz, 1H), 8.18 (ddd, J=8.0, 2.3, 1.6 Hz, 1H), 8.38 (t, J=2.1 Hz, 1H), 8.63 (dd, J=4.9, 1.5 Hz, 1H), 8.72 (d, J=2.2 Hz, 1H), 8.85 (d, J=2.0 Hz, 1H), 8.88 (dd, J=2.4, 0.7 Hz, 1H).

Compound 20—A three-necked round-bottomed flask equipped with a thermometer was charged with compound 19 (1.2 g, 5.1 mmol), toluene (8 mL), THF (3 mL), and triisopropylborate (1.4 mL, 6.0 mmol). After cooling to –40° C. (dry ice/acetone), n-butyllithium (1.6 M in hexanes, 3.75 mL) was slowly added over the course of 30 min. The reaction was then allowed to warm to –20° C., and HCl (2M, 5 mL) was added. When the reaction reached room temperature, the aqueous layer was removed and adjusted to pH 7.6 with NaOH (3M, 2 mL), saturated with NaCl, and extracted with THF (3×6 mL). The THF layers were combined, dried with $MgSO_4$, evaporated to an oil, diluted with $CH_3CN$ (40 mL), and heated at 70° C. for 30 min. The solution was let crystallize at 4° C. for 72 h. The yellow solid was filtered, washed with ice-cold $CH_3CN$, and air-dried (0.38 g, 37%). $^1H$ NMR ($CD_3OD$, 500 MHz) δ 7.61 (dd, J=7.7, 4.9 Hz, 1H), 8.21 (dt, J=8.0, 1.9 Hz, 1H), 8.60 (s, 1H), 8.65 (dd, J=4.9, 1.4 Hz, 1H), 8.72 (s, 1H), 8.89 (d, J=2.2 Hz, 1H), 8.91 (d, J=1.9 Hz, 1H).

Compound 29 via 31—To a suspension of compound 20 (0.37 g, 1.85 mmol) and ethyl-5-bromonicotinate (0.39 g, 1.68 mmol) in anhydrous 1,4-dioxane (20 mL), was added $PPh_3$ (0.1 g, 0.37 mmol) and $Pd(OAc)_2$ (0.02 g, 0.09 mmol) followed by an aqueous solution of $K_3PO_4$ (2 M, 1.65 mL). The reaction was refluxed for 1.5 h. while a gentle and steady stream of argon was bubbled through the solution. After cooling to room temperature, EtOAc (10 mL) was added, and the organic layer was washed with water (10 mL), dried over $MgSO_4$, and evaporated in vacuo to give crude 31 as a yellow solid. To a suspension of this solid in methanol (20 mL) and water (5 mL), was added LiOH (0.12 g, 5.1 mmol), and the reaction was stirred for 4 h. After removal of methanol in vacuo, more water was added (10 mL), and the basic aqueous solution was washed with EtOAc (3×5 mL), then adjusted to pH ~4 with $KHSO_4$ (1 M), which resulted in precipitation. The white precipitate was collected by filtration, washed with acetone and hexanes, and dried to give compound 29 (0.31 g, 67%). $^1H$ NMR (DMSO-$d_6$, 500 MHz) δ 7.56 (ddd, J=7.9, 4.8, 0.8 Hz, 1H), 8.33 (ddd, J=7.9, 2.3, 1.7 Hz, 1H), 8.59 (t, J=2.2 Hz, 1H), 8.66 (dd, J=4.8, 1.6 Hz, 1H), 8.68 (t, J=2.2 Hz, 1H), 9.04 (dd, J=4.1, 2.2 Hz, 2H), 9.12 (m, 2H), 9.26 (d, J=2.3 Hz, 1H).

Compound 32—To a cooled (0° C.) suspension of compound 29 (0.3 g, 1.0 mmol) in dichloromethane (15 mL), was added N-(3-dimethylaminopropyl)-N'-ethylcarbodiimide hydrochloride (0.23 g, 1.2 mmol), 1-hydroxy-benzotriazole hydrate (0.16 g, 1.2 mmol), and triethylamine (0.28 mL, 2.0 mmol). After stirring for 30 min. at 0° C., compound 10 (0.14 g, 0.4 mmol) was added. The reaction was stirred for 24 h. White precipitate formed. After the addition of saturated $NaHCO_3$ (50 mL), a significant amount of solid remained in both layers. The solid was filtered, washed with DCM, $NaHCO_3$, hexanes, and dried to give compound 32 (0.19 g, 61%). $^1H$ NMR ($CD_3OD$, 500 MHz) δ 1.60 (m, 2H), 1.73 (m, 4H), 1.86 (s, 3H), 1.96 (m, 2H), 3.23 (m, 4H), 3.49 (m, 2H), 4.58 (dd, J=9.2, 5.1 Hz, 2H), 5.29 (s, 1H), 5.63 (s, 1H), 7.60 (dd, J=7.6, 5.0 Hz, 2H), 8.26 (m, 2H), 8.46 (s, 1H), 8.49 (s, 1H), 8.53 (s, 1H), 8.63 (d, J=4.6 Hz, 2H), 8.72 (s, 1H), 8.93 (m, 7H), 9.05 (s, 3H).

Compound T-2—2-Bromomethylphenyl boronic acid (0.47 g, 2.2 mmol) was added to a solution of compound 32 (0.19 g, 0.24 mmol) in DMF (4 mL) and ethylene glycol (0.12 mL, 2.2 mmol). The reaction was stirred at 55° C. for 72 h. Acetone (40 mL) was added, and the resulting precipitate was sonicated until a fine pink powder was obtained. The solid was collected by centrifugation, washed with acetone several times and dried under argon (0.30 g, 60%). $^1H$ NMR ($D_2O$, 500 MHz) δ 1.53 (m, 2H), 1.70 (m, 4H), 1.78 (s, 3H), 1.95 (m, 2H), 3.20 (m, 4H), 3.47 (m, 2H), 4.46 (t, 1H), 5.30 (s, 1H), 5.53 (s, 1H), 6.09 (s, 4H), 6.14 (s, 4H), 6.16 (s, 4H), 7.56 (m, 18H), 7.77 (m, 6H), 8.25 (t, 2H), 8.91 (d, J=7.9, 2H), 9.10 (d, 2H), 9.26 (m, 6H), 9.33 (m, 4H), 9.38 (m, 2H), 9.46 (s, 1H), 9.50 (s, 1H).

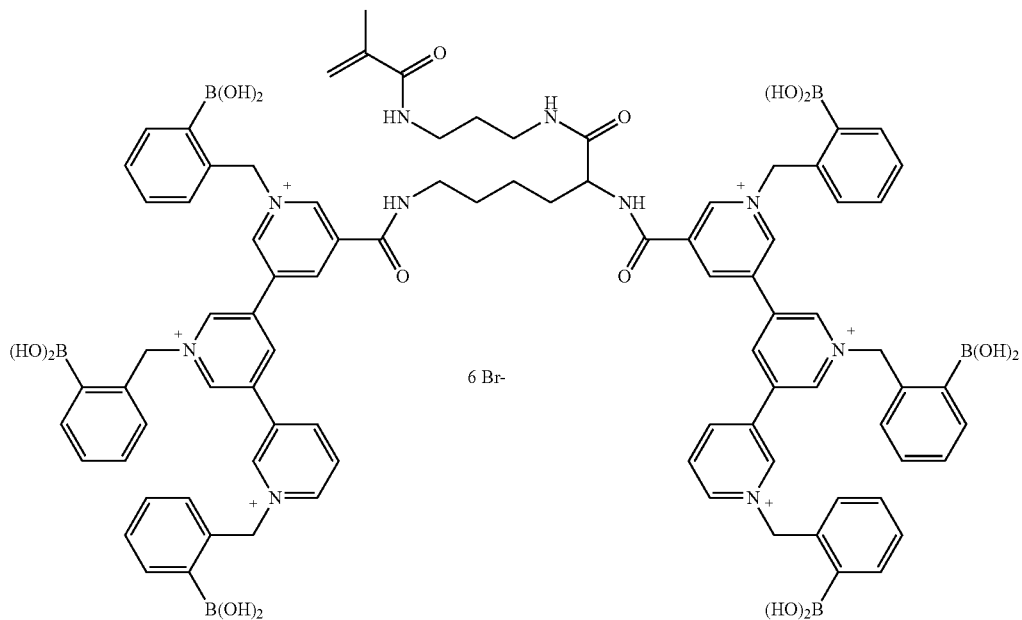

T-2

EXAMPLE 3

Synthesis of P-1

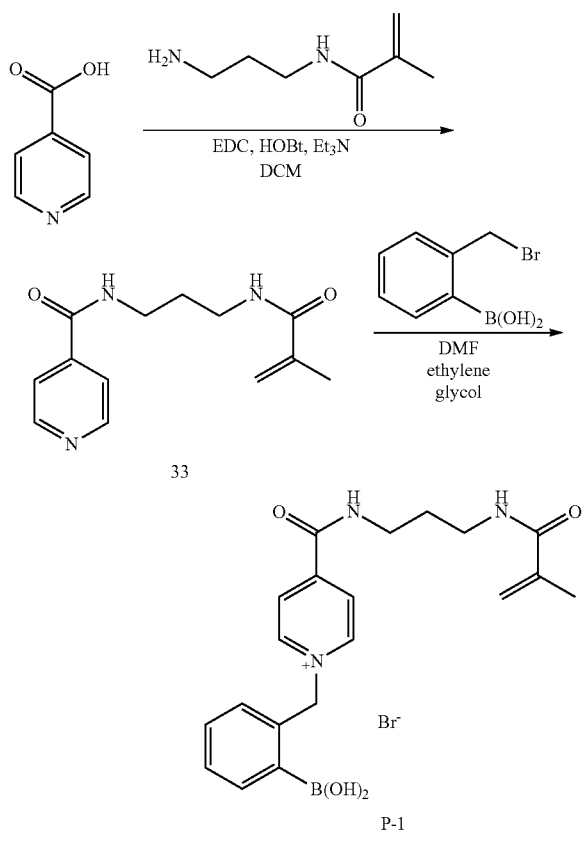

Compound 33—To a cooled (0° C.) suspension of isonicotinic acid (0.57 g, 4.7 mmol) in dichloromethane (80 mL), was added N-(3-dimethylaminopropyl)-N'-ethylcarbodiimide hydrochloride (1.1 g, 5.6 mmol), 1-hydroxy-benzotriazole hydrate (0.76 g, 5.6 mmol), and triethylamine (0.8 mL, 5.6 mmol). After stirring for 30 min. at 0° C., N-(3-aminopropyl) methacrylamide hydrochloride (1.0 g, 5.6 mmol) and triethylamine (0.8 mL, 5.6 mmol) were added. The reaction was stirred for 2 h., then washed with saturated $NaHCO_3$ (3×25 mL). The DCM layer was dried with $MgSO_4$, reduced in volume in vacuo, and purified by flash column chromatography (2%-10% methanol in DCM) to give compound 33 (0.37 g, 32%) as a white solid. $^1$H NMR ($CDCl_3$, 500 MHz) δ 1.77 (m, 2H), 2.01 (s, 3H), 3.47 (q, J=6.5 Hz, 2H), 3.50 (q, J=6.1 Hz, 2H), 5.40 (s, 1H), 5.80 (s, 1H), 6.36 (t, 1H), 7.76 (d, J=6.1 Hz, 2H), 7.90 (t, 1H), 8.76 (d, J=6.1 Hz, 1H).

Compound P-1—2-Bromomethylphenyl boronic acid (0.45 g, 2.1 mmol) was added to a solution of compound 33 (0.19 g, 0.24 mmol) in acetonitrile (75 mL). The reaction was stirred at 50° C. for 16 h. The reaction was concentrated in vacuo until ~5 mL remained. Ether (20 mL) was added, and the precipitate was sonicated, and collected by centrifugation. To remove excess starting material, the white precipitate was sonicated in DCM for 1 h. The DCM was decanted from the oil, and the oil was then sonicated in ether until a white powder was obtained. The solid was collected by centrifugation, washed with ether several times and dried under argon (0.23 g, 36%). $^1$H NMR ($D_2O$, 500 MHz) δ 1.87 (m, 2H), 1.89 (s, 3H), 3.34 (t, J=6.7 Hz, 2H), 3.48 (t, J=6.7 Hz, 2H), 5.40 (s, 1H), 5.65 (s, 1H), 6.03 (s, 2H), 7.55 (m, 3H), 7.76 (d, J=7.1 Hz, 1H), 8.25 (d, J=6.3 Hz, 2H), 8.96 (d, J=6.5 Hz, 1H).

EXAMPLE 4

Synthesis of P-2

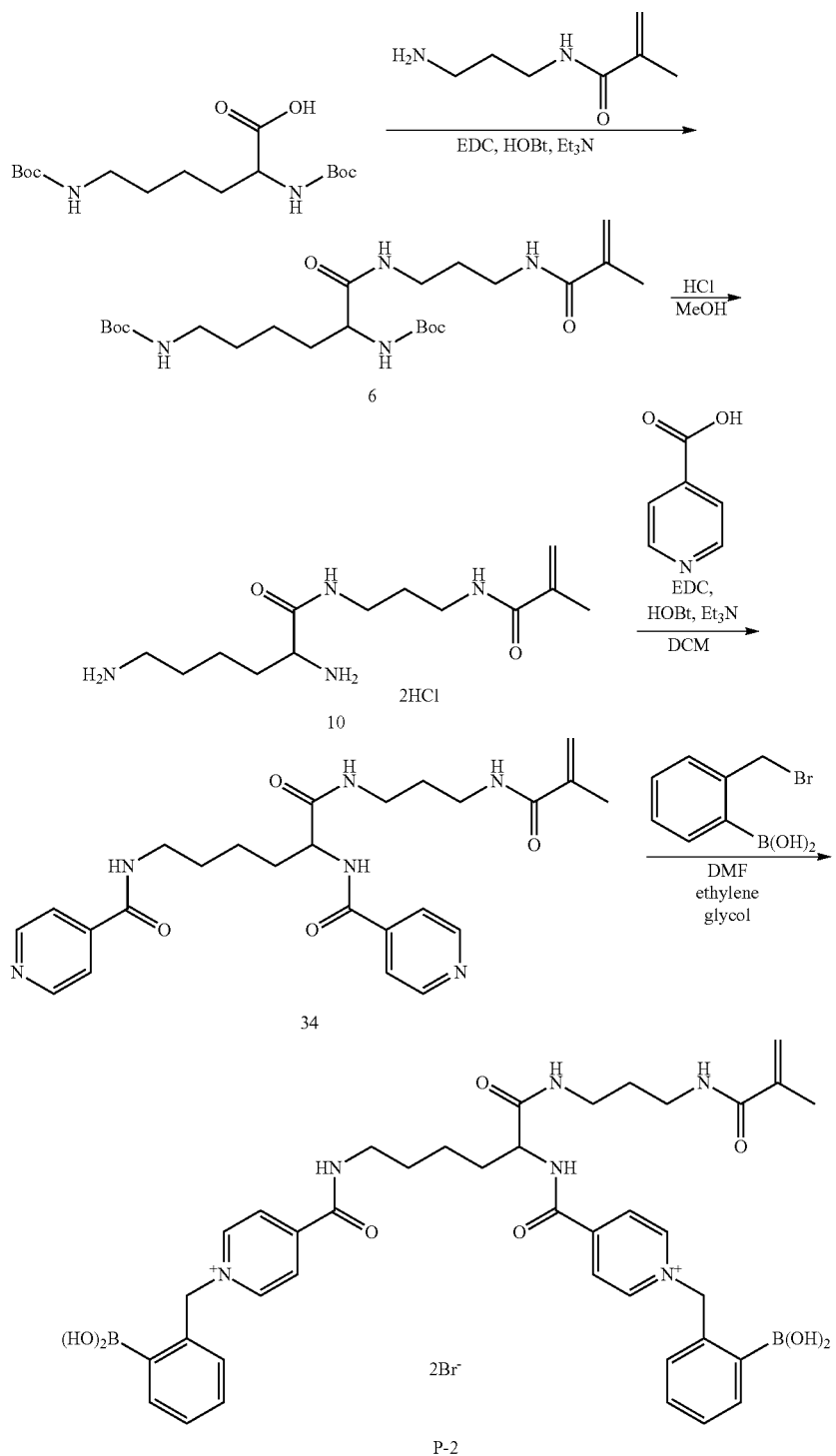

Compound 10—To a cooled (0° C.) solution of N,N-diboc-lysine (dicyclohexylammonium) salt (4.2 g, 8.0 mmol) in dichloromethane (200 mL), was added N-(3-dimethylaminopropyl)-N'-ethylcarbodiimide hydrochloride (1.8 g, 9.6 mmol), 1-hydroxy-benzotriazole hydrate (1.3 g, 9.6 mmol), and triethylamine (1.3 mL, 9.6 mmol). After stirring for 30 min. at 0° C., N-(3-aminopropyl)methacrylamide hydrochloride (1.7 g, 9.6 mmol) and triethylamine (1.3 mL, 9.6 mmol)

were added. The reaction was stirred for 8 h., then washed with saturated NaHCO$_3$ (3×75 mL). The DCM layer was dried with MgSO$_4$, reduced in volume in vacuo, and purified by flash column chromatography (2%-20% methanol in DCM) to give compound 6. TLC: R$_f$=0.71 (10% MeOH/DCM). The appropriate fractions were pooled and concentrated to about 5 mL (not taken to dryness to avoid polymerization), then 1.25 M methanolic HCl (30 mL) was added and the reaction was stirred for 48 h., and concentrated in vacuo to give 10 as a white foam (2.1 g, 78%). $^1$H NMR (D$_2$O, 500 MHz) δ 1.44 (p, J=8.3 Hz, 2H), 1.71 (p, J=7.8 Hz, 2H), 1.78 (p, J=6.9 Hz, 2H), 1.90 (m, 2H), 1.92 (s, 3H), 3.00 (t, J=7.7 Hz, 2H), 3.29 (m, 4H), 3.95 (t, J=6.7 Hz, 1H), 5.44 (s, 1H), 5.67 (s, 1H).

Compound 34—Compound 10 (0.4 g, 1.2 mmol) was suspended in a solution of dichloromethane (50 mL) and triethylamine (0.9 mL, 6.4 mmol) and cooled to 0° C. Then, isonicotinic acid (0.4 g, 3.2 mmol), N-(3-dimethylaminopropyl)-N'-ethylcarbodiimide hydrochloride (0.73 g, 3.8 mmol), 1-hydroxy-benzotriazole hydrate (0.51 g, 3.8 mmol), and triethylamine (0.9 mL, 6.4 mmol) were added. After stirring for 1 h. at 0° C., the reaction was sonicated for 3 h. to help dissolve the solids. After washing with saturated NaHCO$_3$ (3×75 mL), the DCM layer was dried with MgSO$_4$, reduced in volume in vacuo, and purified by flash column chromatography (2%-20% methanol in DCM, silica gel pretreated with 1% triethylamine) to give compound 34 (19 mg, 3%). TLC: R$_f$=0.59 (15% MeOH/DCM, plate pretreated with triethylamine).

Compound P-2—2-Bromomethylphenyl boronic acid (0.02 g, 0.1 mmol) was added to a solution of compound 34 (18.7 mg, 40 μmol) in DMF (1 mL). The reaction was stirred at 55° C. for 72 h. Diethylether (20 mL) was added to separate the product as an oil. The solvent was decanted, and the remaining oil was sonicated in ether until it became a beige powder. The solid was collected by centrifugation, washed with ether several times and dried under argon (35 mg, 96%). $^1$H NMR (D$_2$O, 500 MHz) δ 1.46 (m, 2H), 1.69 (m, 4H), 1.86 (s, 3H), 1.90 (m, 2H), 3.22 (m, 4H), 3.44 (t, J=6.8 Hz, 2H), 4.42 (t, J=7.4 Hz, 1H), 5.38 (s, 1H), 5.61 (s, 1H), 6.02 (s, 2H), 6.03 (s, 2H), 7.56 (m, 6H), 7.76 (d, J=7.6 Hz, 2H), 8.23 (d, J=6.7 Hz, 2H), 8.28 (d, J=6.7 Hz, 2H), 8.97 (m, 4H).

EXAMPLE 5

Synthesis of P-3

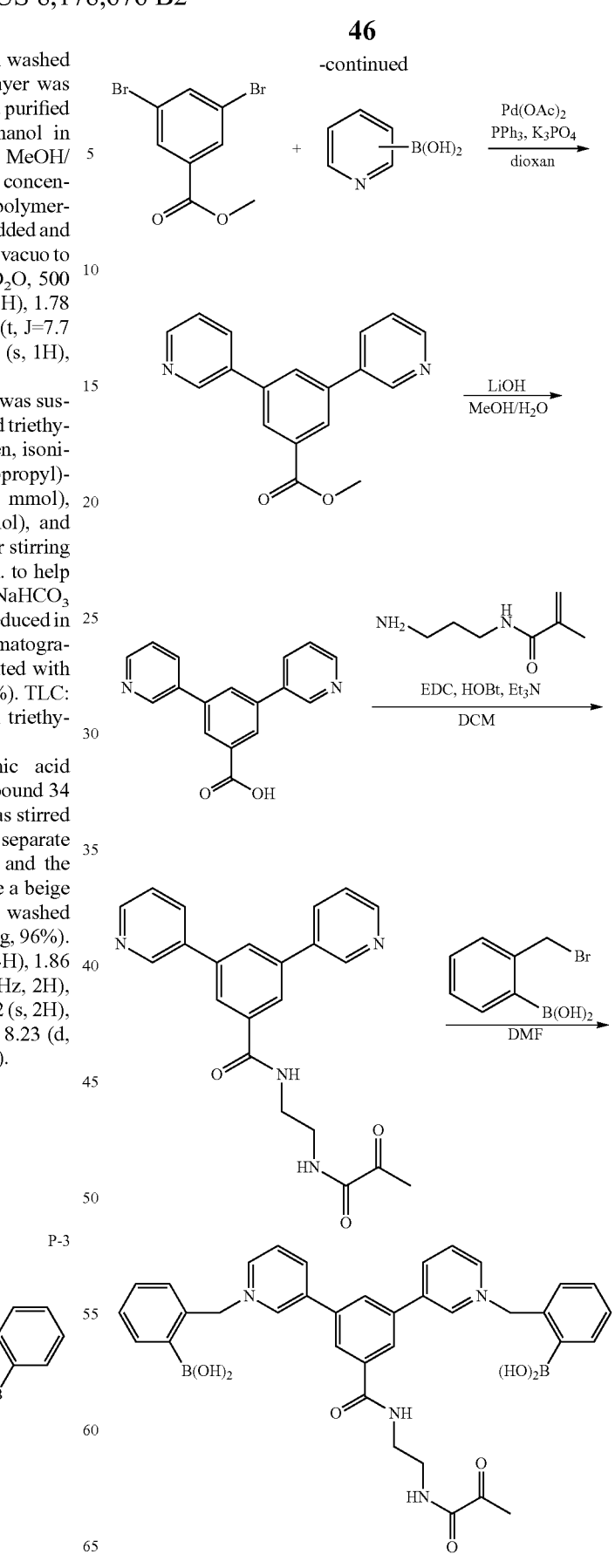

P-3

EXAMPLE 6
Synthesis of P-4
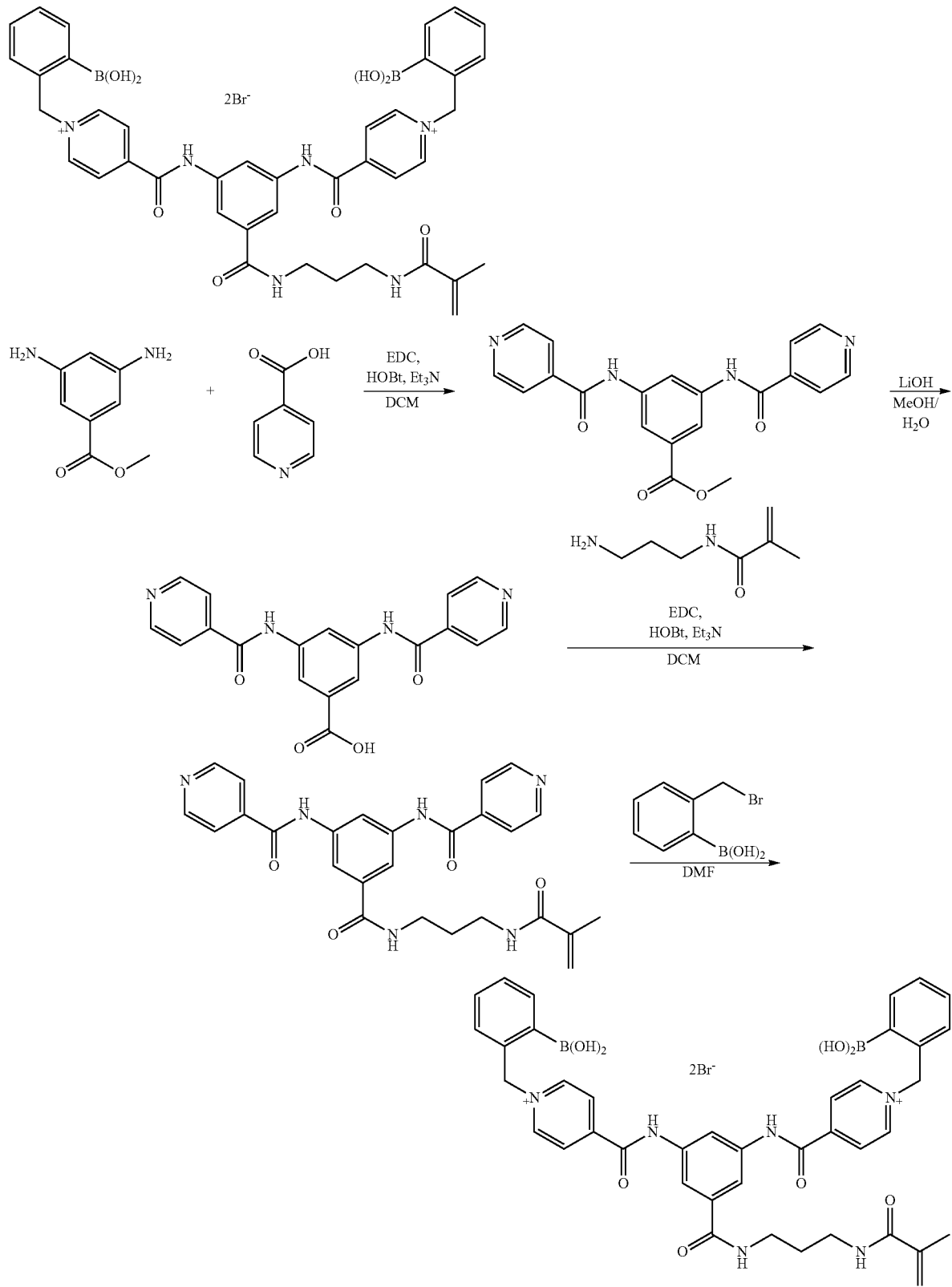

EXAMPLE 7

Sensor Preparation and Testing

The quencher, P-1, was dissolved in 41.4 μL of a stock solution containing N,N'-dimethylacrylamide (100 mg) and N,N'-methylenebismethacrylamide (2 mg). This quencher solution (20.7 μL) was then added to a solution containing HPTS-TriCys-MA (50 μL of a 2 mM aqueous solution), HCl (20 μL of a 100 mM solution), 2,2'-azobis[2-(2-imidazolin-2-yl)propane]dihydrochloride (10 μL, of a 40 mg/mL solution), and DI water (99.3 μL). Some of this solution was then polymerized onto the tip of a fiber optic sensor by heating at 37° C. for 24 h. to form a hydrogel.

The sensor was tested by placing it in solutions containing different glucose concentrations ranging from 0 mg/dL to 400 mg/dL. The hydrogel indicator chemistry at the tip of the optical fiber was excited with light at a wavelength of 470 nm. Fluorescence emission was monitored between 520-700 nm. The results are illustrated in FIG. 1.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. The compound:

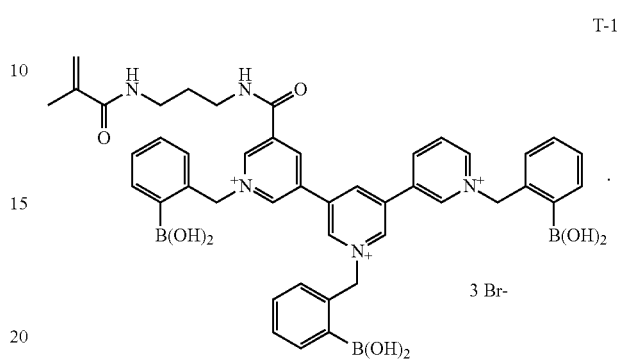

2. A method of making the compound of claim 1, comprising the steps of:

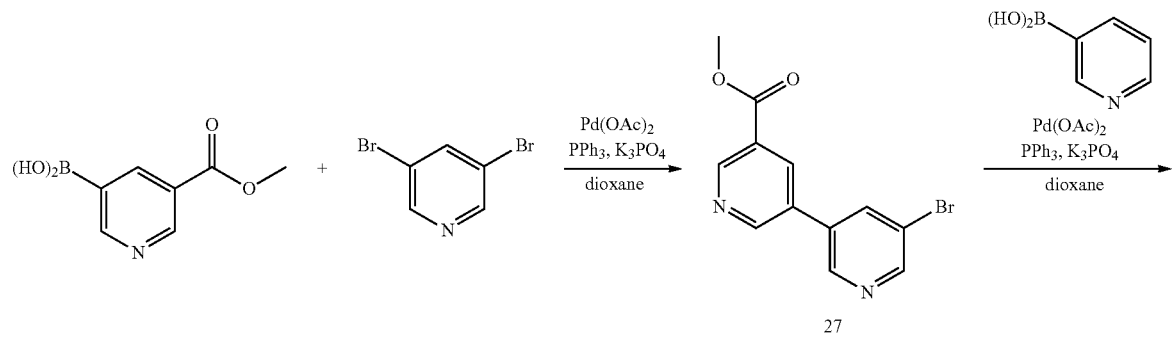

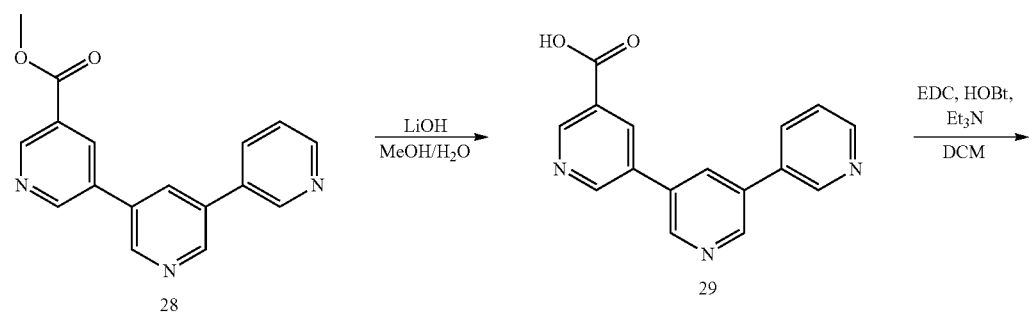

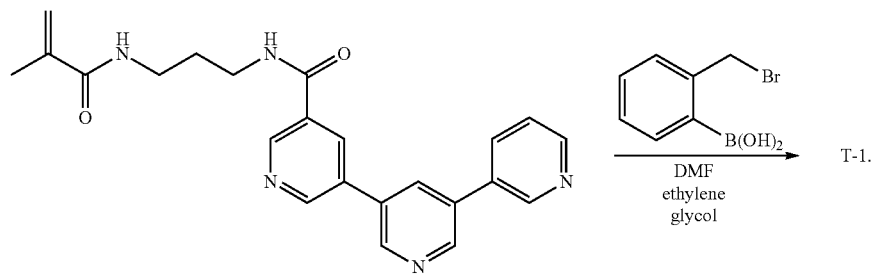

3. The compound:
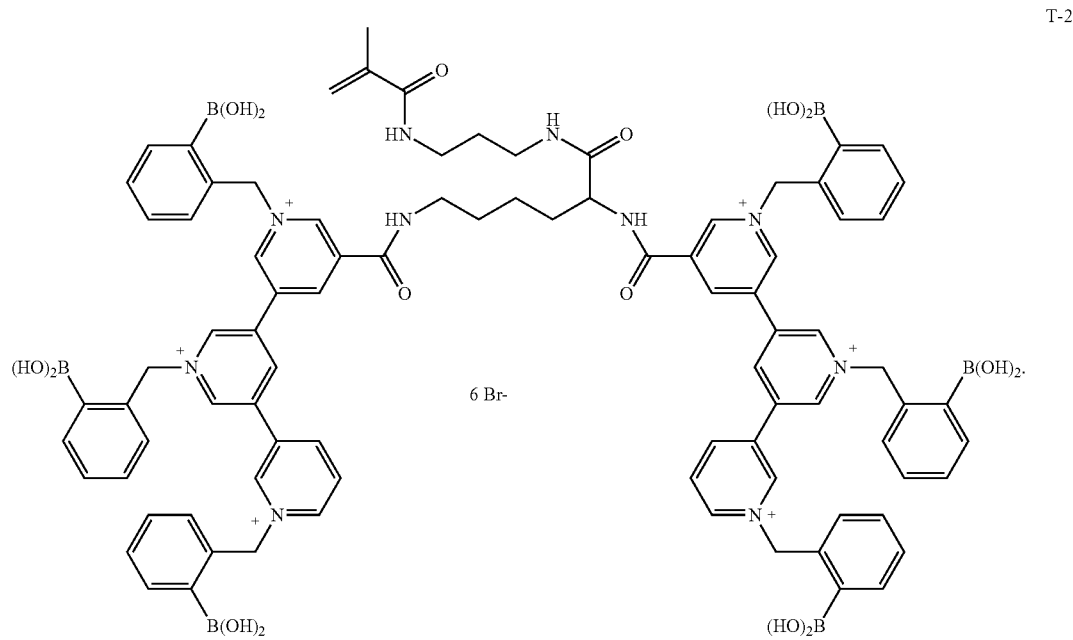
T-2
6 Br−
4. A method of making the compound of claim 3, comprising the steps of:
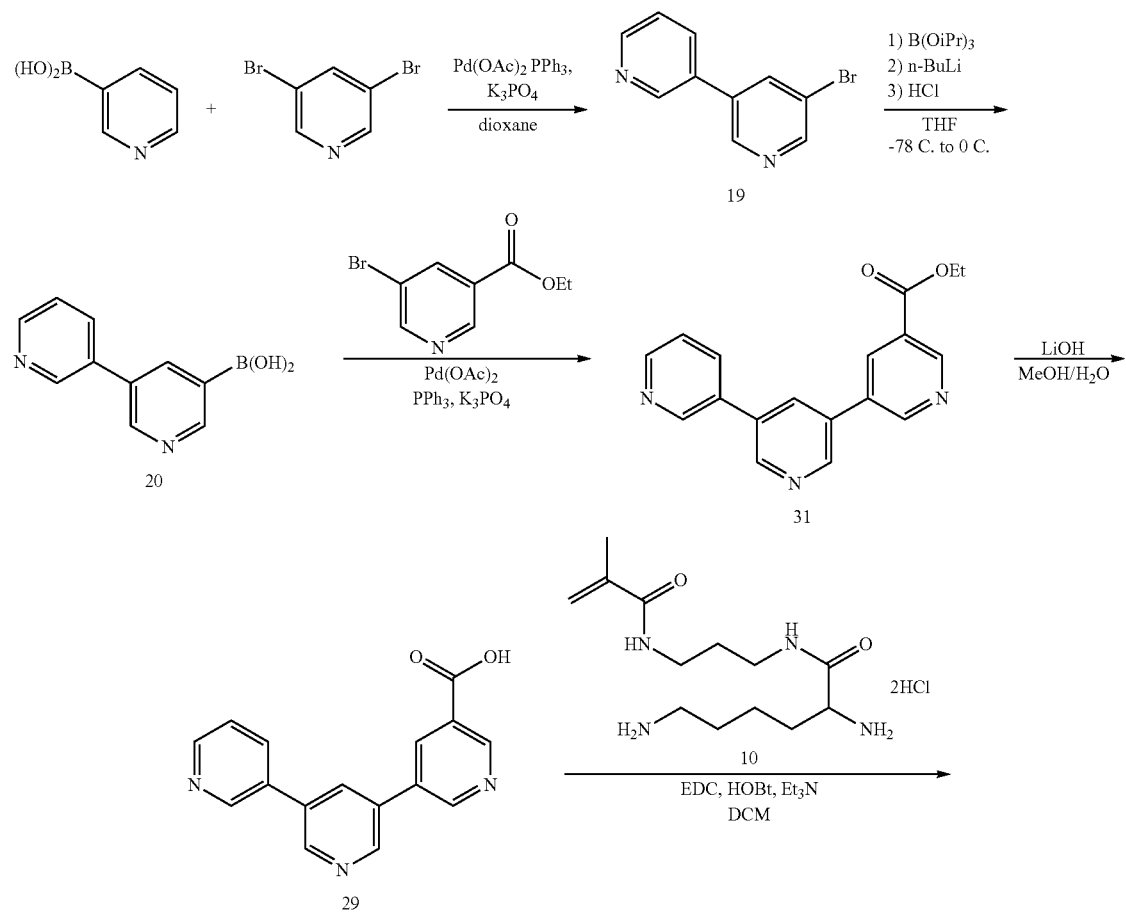

-continued

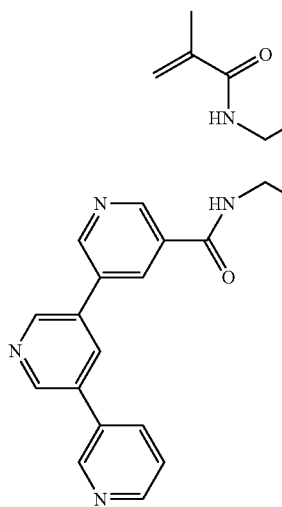 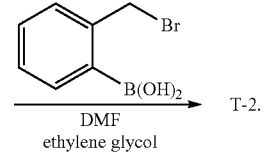 T-2.

DMF
ethylene glycol

32

5. A glucose sensor comprising the compound of claim 1 and a fluorescent dye.

6. The glucose sensor of claim 5, wherein said compound is in the form of a polymer.

7. The glucose sensor of claim 5, further comprising a glucose permeable immobilizing means.

8. The glucose sensor of claim 7, wherein said glucose permeable immobilizing means is a polymer matrix or a semipermeable membrane.

9. A glucose sensor comprising the compound of claim 3 and a fluorescent dye.

10. The glucose sensor of claim 9, wherein said compound is in the form of a polymer.

11. The glucose sensor of claim 9, further comprising a glucose permeable immobilizing means.

12. The glucose sensor of claim 11, wherein said glucose permeable immobilizing means is a polymer matrix or a semipermeable membrane.

* * * * *